(12) United States Patent
Ko et al.

(10) Patent No.: US 8,629,096 B2
(45) Date of Patent: Jan. 14, 2014

(54) COMPOSITIONS COMPRISING FUNGAL IMMUNOMODULATORY PROTEIN AND USE THEREOF

(75) Inventors: Jiunn-Liang Ko, Taichung (TW); Tzu-Chih Chen, Taipei (TW)

(73) Assignee: Yeastern Biotech Co., Ltd., Taipei (TW)

( * ) Notice: Subject to any disclaimer, the term of this patent is extended or adjusted under 35 U.S.C. 154(b) by 0 days.

(21) Appl. No.: 13/422,789

(22) Filed: Mar. 16, 2012

(65) Prior Publication Data

US 2012/0177674 A1 Jul. 12, 2012

Related U.S. Application Data

(63) Continuation of application No. 12/497,898, filed on Jul. 6, 2009, which is a continuation-in-part of application No. 11/233,364, filed on Sep. 23, 2005.

(51) Int. Cl.
  *A61K 38/00* (2006.01)
  *A61P 35/00* (2006.01)
  *A61K 38/16* (2006.01)

(52) U.S. Cl.
  USPC ......... 514/1.1; 514/19.2; 514/19.3; 514/19.4; 514/19.5; 514/21.2

(58) Field of Classification Search
  None
  See application file for complete search history.

(56) References Cited

U.S. PATENT DOCUMENTS 6,316,002 B1 * 11/2001 Liu et al. .................. 424/195.15
8,163,519 B2 * 4/2012 Ko et al. ...................... 435/69.1

FOREIGN PATENT DOCUMENTS

JP 0203206 A * 2/1990 ............. A61K 35/84

OTHER PUBLICATIONS

Tanaka et al. (J. Biol. Chem. 264:16372-16377(1989)).*

* cited by examiner

*Primary Examiner* — Peter J Reddig
(74) *Attorney, Agent, or Firm* — WPAT, P.C.; Anthony King

(57) ABSTRACT

This invention relates to a method for stimulation or an activation of immunological function directed to activate natural killer cells and macrophages or increase production of serum antibody in a patient in need of such stimulation or activation, comprising administering an isolated and/or purified polypeptide of a fungal immunomodulatory protein. This invention also relates to a method for suppressing proliferation of a cancer cell and a method for suppressing a tumor cell mobility, comprising providing to the tumor cell a purified polypeptide of a fungal immunomodulatory protein.

9 Claims, 15 Drawing Sheets

(A)

(B)

(A)

Fip-*gts* (µg/ml)

(B)

Fip-*gts* concentration (µg/ml)

(B)

Figure 1:
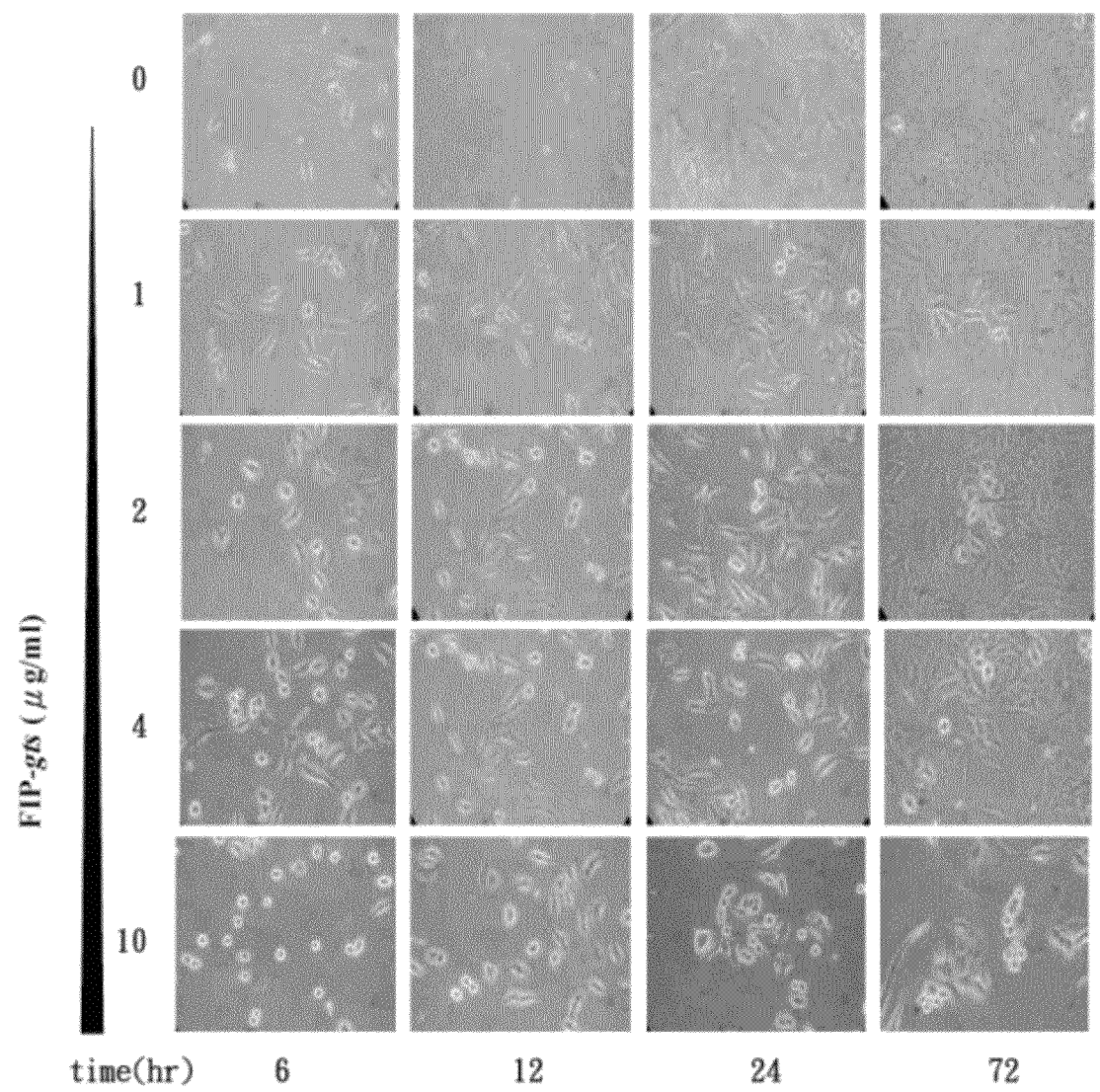

|  | Time | Control | FIP-gts (μg/ml) | | | |
|---|---|---|---|---|---|---|
|  |  |  | 1 | 2 | 4 | 10 |
| G1 phase | 24 hr | 58.2±3.5 | 59.9±3.0 | 62.0±4.3 | 64.0±6.2 | 75.5±5.8 |
| (%) | 48 hr | 60.6±4.6 | 68.8±0.3 | 72.6±2.5* | 76.1±5.3* | 82.1±2.7* |
| S phase | 24 hr | 32.8±2.5 | 30.9±2.4 | 30.1±2.9 | 27.2±2.4 | 18.6±3.2 |
| (%) | 48 hr | 31.8±5.2 | 25.1±0.7 | 23.0±0.1 | 20.0±3.7 | 13.8±2.3 |
| G2/M phase | 24 hr | 9.1±1.1 | 9.0±2.5 | 7.9±1.9 | 8.3±3.8 | 5.9±3.1 |
| (%) | 48 hr | 7.6±0.7 | 5.1±0.4 | 4.4±2.6 | 4.0±1.5 | 3.8±0.4 |
| SubG1 phase | 24 hr | 0.2±0.27 | 0.3±0.22 | 0.4±0.22 | 0.4±0.32 | 0.9±0.35 |
| (%) | 48 hr | 0.2±0.05 | 0.5±0.33 | 0.4±0.08 | 0.6±0.42 | 1.6±0.82 |

(A)

(B)

(A)

(B)

(A)

(B)

SEQUENCE LISTING

<160> NUMBER OF SEQ ID NOS: 19

<210> SEQ ID NO 1
<211> LENGTH: 111
<212> TYPE: PRT
<213> ORGANISM: Ganoderma specisis
<220> FEATURE:
<221> NAME/KEY: PEPTIDE
<222> LOCATION: (1)..(111)

<400> SEQUENCE: 1

Met Ser Asp Thr Ala Leu Ile Phe Arg Leu Ala Trp Asp Val Lys Lys
1               5                   10                  15

Leu Ser Phe Asp Tyr Thr Pro Asn Trp Gly Arg Gly Asn Pro Asn Asn
                20                  25                  30

Phe Ile Asp Thr Val Thr Phe Pro Lys Val Leu Thr Asp Lys Ala Tyr
            35                  40                  45

Thr Tyr Arg Val Ala Val Ser Gly Arg Asn Leu Gly Val Lys Pro Ser
        50                  55                  60

Tyr Ala Val Glu Ser Asp Gly Ser Gln Lys Val Asn Phe Leu Glu Tyr
65                  70                  75                  80

Asn Ser Gly Tyr Gly Ile Ala Asp Thr Asn Thr Ile Gln Val Phe Val
                85                  90                  95

Val Asp Pro Asp Thr Asn Asn Asp Phe Ile Ile Ala Gln Trp Asn
            100                 105                 110

<210> SEQ ID NO 2
<211> LENGTH: 20
<212> TYPE: DNA
<213> ORGANISM: Artificial Sequence
<220> FEATURE:
<223> OTHER INFORMATION: MMP-2-1
<220> FEATURE:
<221> NAME/KEY: misc_feature
<222> LOCATION: (1)..(20)
<223> OTHER INFORMATION: synthesized

<400> SEQUENCE: 2
ggccctgtca ctcctgagat                                              20

<210> SEQ ID NO 3
<211> LENGTH: 20
<212> TYPE: DNA

```
<213> ORGANISM: Artificial Sequence
<220> FEATURE:
<223> OTHER INFORMATION: MMP-2-2
<220> FEATURE:
<221> NAME/KEY: misc_feature
<222> LOCATION: (1)..(20)
<223> OTHER INFORMATION: synthesized

<400> SEQUENCE: 3
ggcatccagg ttatcgggga                                          20

<210> SEQ ID NO 4
<211> LENGTH: 27
<212> TYPE: DNA
<213> ORGANISM: Artificial Sequence
<220> FEATURE:
<223> OTHER INFORMATION: PAI-1-1
<220> FEATURE:
<221> NAME/KEY: misc_feature
<222> LOCATION: (1)..(27)
<223> OTHER INFORMATION: synthesized

<400> SEQUENCE: 4
ggatccagcc actggaaagg caacatg                                  27

<210> SEQ ID NO 5
<211> LENGTH: 27
<212> TYPE: DNA
<213> ORGANISM: Artificial Sequence
<220> FEATURE:
<223> OTHER INFORMATION: PAI-1-2
<220> FEATURE:
<221> NAME/KEY: misc_feature
<222> LOCATION: (1)..(27)
<223> OTHER INFORMATION: synthesized

<400> SEQUENCE: 5
ggatccgtgc cggaccacaa agaggaa                                  27

<210> SEQ ID NO 6
<211> LENGTH: 21
<212> TYPE: DNA
<213> ORGANISM: Artificial Sequence
<220> FEATURE:
<223> OTHER INFORMATION: TIMP-1-1
<220> FEATURE:
<221> NAME/KEY: misc_feature
<222> LOCATION: (1)..(21)
<223> OTHER INFORMATION: synthesized

<400> SEQUENCE: 6
tggagagaca ctgccaactt g                                        21

<210> SEQ ID NO 7
<211> LENGTH: 20
<212> TYPE: DNA
<213> ORGANISM: Artificial Sequence
<220> FEATURE:
<223> OTHER INFORMATION: TIMP-1-2
<220> FEATURE:
<221> NAME/KEY: misc_feature
<222> LOCATION: (1)..(20)
<223> OTHER INFORMATION: synthesized

<400> SEQUENCE: 7
aggctgtgcc ttcctacaga                                          20

<210> SEQ ID NO 8
<211> LENGTH: 18
<212> TYPE: DNA
```

```
<213> ORGANISM: Artificial Sequence
<220> FEATURE:
<223> OTHER INFORMATION: TS
<220> FEATURE:
<221> NAME/KEY: misc_feature
<222> LOCATION: (1)..(18)
<223> OTHER INFORMATION: synthesized

<400> SEQUENCE: 8
aatccgtcga gcagagtt                                                 18

<210> SEQ ID NO 9
<211> LENGTH: 30
<212> TYPE: DNA
<213> ORGANISM: Artificial Sequence
<220> FEATURE:
<223> OTHER INFORMATION: ACX
<220> FEATURE:
<221> NAME/KEY: misc_feature
<222> LOCATION: (1)..(30)
<223> OTHER INFORMATION: synthesized

<400> SEQUENCE: 9
gcgcggctta cccttaccct taccctaacc                                    30

<210> SEQ ID NO 10
<211> LENGTH: 18
<212> TYPE: DNA
<213> ORGANISM: Artificial Sequence
<220> FEATURE:
<223> OTHER INFORMATION: NT
<220> FEATURE:
<221> NAME/KEY: misc_feature
<222> LOCATION: (1)..(18)
<223> OTHER INFORMATION: synthesized

<400> SEQUENCE: 10
atcgcttctc ggccttt                                                  18

<210> SEQ ID NO 11
<211> LENGTH: 36
<212> TYPE: DNA
<213> ORGANISM: Artificial Sequence
<220> FEATURE:
<223> OTHER INFORMATION: TSNT
<220> FEATURE:
<221> NAME/KEY: misc_feature
<222> LOCATION: (1)..(36)
<223> OTHER INFORMATION: synthesized

<400> SEQUENCE: 11
aatccgtcga gcagagttaa aaggccgaga agcgat                             36

<210> SEQ ID NO 12
<211> LENGTH: 23
<212> TYPE: DNA
<213> ORGANISM: Artificial Sequence
<220> FEATURE:
<223> OTHER INFORMATION: hTERT sense
<220> FEATURE:
<221> NAME/KEY: misc_feature
<222> LOCATION: (1)..(23)
<223> OTHER INFORMATION: synthesized

<400> SEQUENCE: 12
agttcctgca ctggctgatg agt                                           23

<210> SEQ ID NO 13
<211> LENGTH: 21
<212> TYPE: DNA
```

```
<213> ORGANISM: Artificial Sequence
<220> FEATURE:
<223> OTHER INFORMATION: hTERT antisense
<220> FEATURE:
<221> NAME/KEY: misc_feature
<222> LOCATION: (1)..(21)
<223> OTHER INFORMATION: synthesized

<400> SEQUENCE: 13
ctcggccctc ttttctctgc g                                              21

<210> SEQ ID NO 14
<211> LENGTH: 26
<212> TYPE: DNA
<213> ORGANISM: Artificial Sequence
<220> FEATURE:
<223> OTHER INFORMATION: hTR sense
<220> FEATURE:
<221> NAME/KEY: misc_feature
<222> LOCATION: (1)..(26)
<223> OTHER INFORMATION: synthesized

<400> SEQUENCE: 14
tctaacccta actgagaagg gcgtag                                         26

<210> SEQ ID NO 15
<211> LENGTH: 26
<212> TYPE: DNA
<213> ORGANISM: Artificial Sequence
<220> FEATURE:
<223> OTHER INFORMATION: hTR antisense
<220> FEATURE:
<221> NAME/KEY: misc_feature
<222> LOCATION: (1)..(26)
<223> OTHER INFORMATION: synthesized

<400> SEQUENCE: 15
gtttgctcta gaatgaacgg tggaag                                         26

<210> SEQ ID NO 16
<211> LENGTH: 19
<212> TYPE: DNA
<213> ORGANISM: Artificial Sequence
<220> FEATURE:
<223> OTHER INFORMATION: beta-actin sense
<220> FEATURE:
<221> NAME/KEY: misc_feature
<222> LOCATION: (1)..(19)
<223> OTHER INFORMATION: synthesized

<400> SEQUENCE: 16
cagggagtga tggtgggca                                                 19

<210> SEQ ID NO 17
<211> LENGTH: 24
<212> TYPE: DNA
<213> ORGANISM: Artificial Sequence
<220> FEATURE:
<223> OTHER INFORMATION: beta-actin antisense
<220> FEATURE:
<221> NAME/KEY: misc_feature
<222> LOCATION: (1)..(24)
<223> OTHER INFORMATION: synthesized

<400> SEQUENCE: 17
caaacatcat ctggtcatct tctc                                           24

<210> SEQ ID NO 18
<211> LENGTH: 39
<212> TYPE: DNA
```

```
<213> ORGANISM: Artificial Sequence
<220> FEATURE:
<223> OTHER INFORMATION: hTERT-E-box sense
<220> FEATURE:
<221> NAME/KEY: misc_feature
<222> LOCATION: (1)..(39)
<223> OTHER INFORMATION: synthesized

<400> SEQUENCE: 18
gggctagcgc gctccccacg tggcggaggg aaagcttcc                              39

<210> SEQ ID NO 19
<211> LENGTH: 39
<212> TYPE: DNA
<213> ORGANISM: Artificial Sequence
<220> FEATURE:
<223> OTHER INFORMATION: hTERT-E-box antisense
<220> FEATURE:
<221> NAME/KEY: misc_feature
<222> LOCATION: (1)..(39)
<223> OTHER INFORMATION: synthesized

<400> SEQUENCE: 19
ggaagctttc cctccgccac gtggggagcg cgctagccc                              39
```

COMPOSITIONS COMPRISING FUNGAL IMMUNOMODULATORY PROTEIN AND USE THEREOF

CROSS REFERENCE TO RELATED APPLICATIONS

This application is a continuation-in-part under 35 U.S.C. §120 of U.S. application Ser. No. 12/497,898, filed on Jul. 6, 2009, now abandoned which is a continuation-in-part of U.S. application Ser. No. 11/233,364, filed on Sep. 23, 2005 now abandoned.

The Sequence Listing is submitted on one ASCII text file and the material on the ASCII text file is hereby incorporated by reference in its entity. The ASCII text file contains a filed named "1091-YB-US-SEQUENCE_ST25", which was created on Mar. 12, 2012 and is 16.155 kilobytes.

FIELD OF THE INVENTION

This present invention relates to fungal immunomodulatory proteins, compositions and method for use in immunotherapy. The present invention also relates to a kit for use in detecting the cancer.

DESCRIPTION OF THE PRIOR ART

Ganoderma is a rare and valuable herb in Chinese medicine. It has been known in China for over 5,000 years as "Ling Zhi". There are a variety of ganodermas, including G. lucidum (red), G. applanatum (brown), G. tsugae (red), G. sinense (black), and G. oregonense (dark brown).

It has been known that Ling Zhi has anti-allergy (Chen H. Y et al., J. Med. Mycol. 1992; 33:505-512), hepatoprotective (Lin J. M. et al., Am J Chin Med. 1993; 21(1):59-69) and anti-tumor effects (Wasser S P, Crit. Rev Immunol 1999. 19:65-96) and immune advantages (Kino, J. Biol. Chem. 1989. 264(1): 472-8). However, Ling Zhi is used restrictedly in the form of extract of raw material (Horner W. E. et al., Allergy 1993; 48:110-116) or small molecules (Kawagishi H., et al., Phytochemistry 1993; 32: 239-241).

Several proteins from edible fungi such as Ganoderma Lucidium (Ling zhi or Reishi), Volvariella Volvacea (Chinese Mushroom), Flammulina Velutipes (Golden needle mushroom) share similar amino acid sequences and immunomodulatory functions. These proteins were named fungal immunomodulatory proteins (FIPs) (Ko J. L., Eur. J. Biochem. 1995; 228:224-249).

In 1989 Kino et al found protein Ling Zhi-8 in G. lucidum (Kino K. et al., J. Biol. Chem. 1989; 264(1): 472-8). LZ-8 has positive effects on systemic anaphylaxis, and has been used for the treatment of liver cancer and preventing diabetes. LZ-8 and another immunomodulatory protein, FIP-fve, obtained from Flammulina Velutipes, have amino acid sequences and folding structures similar to the heavy chain of immunoglobulin. Further, it has been shown that by enhancing the expression of LZ-8, these proteins show immunomodulatory activities and have positive effects on patients with systemic anaphylaxis (Ko J. L., Eur. J. Biochem. 1995; 228:224-249). It was further discovered that FIP can activate human peripheral blood mononuclear cells (HPBMCs), enhance the proliferation of HPBMCs and mouse splenocyte (van der Hem, et al., Transplantation, 1995. 60, 438-443.). Using $^3$H-thymidine to measure the effect of FIP-gts on proliferation, it was further discovered that compared to PHA, 5 µg/ml of FIP-gts or 100 µg/ml FIP-fve is sufficient to reach the maximum proliferation of human lymphocytes (Hsu, C., cited supra). Concerning non-B and non-T cells, it was found that FIP-gts could only promote the proliferation of Non-B cells.

Similar to PHA (phytoagglutinin) and other lectin mitogens, LZ-8 is mitogenic. LZ-8 primarily proliferates T cells with the help of monocyte. A new family of fungal immunomodulatory proteins (FIPs) (Ko J L, et al., Eur J Biochem 1995; 228(2):244-249.) has recently been identified. Four FIPs have been isolated and purified from Ganoderma lucidum, Flammulina veltipes, Volvariella volvacea and Ganoderma tsugae and designated LZ-8, FIP-fve, FIP-vvo and FIP-gts, respectively (Hsu H C, et al., Biochem J 1997; 323 (Pt 2):557-565.). FIPs are mitogenic in vitro for human peripheral blood lymphocytes (hPBLs) and mouse splenocytes. They induce a bell-shaped dose-responsive curve similar to that of lectin mitogens. Activation of hPBLs with FIPs results in the increased production of molecules of IL-2, IFN-γ and tumor necrosis factor-α associated with ICAM-1 expression (Wang P H, et al., J Agric Food Chem 2004; 52(9):2721-2725.). FIPs can also act as immunosuppressive agents. In vivo these proteins can prevent systemic anaphylactic reactions and significantly decrease footpad edema during Arthus reaction in mouse. These observations suggest that FIPs are both health promoting and therapeutic. Although the immunomodulatory activities of FIPs have been researched extensively, their anticancer function has only rarely been explored.

Lin et al have also purified an immunomodulatory protein from the mycelium of Ganoderma tsugae, named FIP-gts (Lin, W. H., et al., J Biol. Chem. 1997. 272, 20044-20048.). The FIP-gts found in the fruit body of Ganoderma tsugae has no immunomodulatory effect; only the protein found in the mycelium has the effect. After cloning, the DNA sequence of FIP-gts was found to be identical to the sequence of LZ-8 in Ganoderma lucidium. Both proteins exhibited the same immunoactivity, demonstrating that they are the same protein.

Analyzing the secondary structure with Garnier analysis, FIP-gts was predicted to have two α-helices, seven β-sheets and one β-turn. The molecular weight of FIP-gts was determined to be 13 kD using SDS-PAGE analysis. Connecting the amino acids with 20 µM glutaraldegyde (protein conjugate), FIP-gts was found to form a 26 kD homodimer.

In addition, three fungal proteins were found by Blast-formation stimulatory activity assay (BFSA). Except proteins found in Ganoderma lucidium, blood clotting proteins found in Flammulina velutipes and Volvariella volvacea have partial immunomodulate activity. Their molecular weights were around 13 kD, and neither of them contains histidine, cysteine or methionine. They are a kind of lectins that are linked to carbohydrates.

Natural Killer (NK) cells are yet another type of lethal lymphocyte. Like cytotoxic T cells, they contain granules filled with potent chemicals. They are called "natural" killers because they, unlike cytotoxic T cells, do not need to recognize a specific antigen before swinging into action. They target tumor cells and protect against a wide variety of infectious microbes. In several immunodeficiency diseases, including AIDS, natural killer cell function is abnormal. Natural killer cells may also contribute to immunoregulation by secreting high levels of influential lymphokines.

Both cytotoxic T cells and natural killer cells kill on contact. The killer binds to its target, aims its weapons, and then delivers a lethal burst of chemicals that produces holes in the target cell's membrane. Fluids seep in and leak out, and the cell bursts.

Until recently, immuno-anti-cancer therapy consisted of three forms: operations, chemotherapy, or radiation. In all these forms, however, resulting side effects were frequent and harmful. Thus, these three forms are not the best way for cancer patients, especially those people in the end stages of cancer. Overdoses of chemotherapy and radiation, for example, could actually prove harmful and shorten lives.

In recent years, however, a fourth anti-cancer immunotherapy has become popular. This fourth way actually strengthens each patient's own natural anti-cancer immuno-power. This fourth way uses the body's own NK (natural killer) cells, which are the strongest and most effective immune cells in the body. There are almost 50,000 times stronger than Killer T-cell, This NK immuno-therapy would undoubtedly become more and more popular in the future.

NK cells constitute an important component of the innate immune system, providing surveillance against certain viruses, intracellular bacteria and transformed cells (Trinchieri G. Adv Immunol 1989; 47:187 376.; French A R, Yokoyama W M. Curr Opin Immunol 2003; 15:45 51.; Smyth M J et al., Nat Immunol 2001; 2:293 9.). NK cells exert cell-mediated cytotoxicity and stand as a bridge between innate and adaptive immune responses through the release of various cytokines (such as IFNg, GM-CSF and TNF-h) and chemokines (e.g. MIP-1 family and RANTES) (Biron C A. Curr Opin Immunol 1997; 9:24 34.; Biron C A et al., Annu Rev Immunol 1999; 17:189 220.). Unlike T cells, NK cell killing of virus-infected or malignant transformed cells do not need pre-sensitization and is independent of MHC restriction, thus NK cells are considered as promising candidates for adoptive transfer treatment of malignant tumors, especially those of the haematopoietic origin (Robertson M J, Ritz J. Blood 1990; 76:2421 38.). Tumor cells that lose or express altered MHC class I antigen escape detection by cytotoxic CD8+ T cells, but they are likely susceptible to be eliminated by NK cells. However, malignant cells often have developed strategies that counteract immune surveillance of the hosts, including down-regulation of MHC class I molecules to avoid immune recognition, increased expression of Fas-L to kill responsive lymphocytes and production of suppressive cytokines such as TGF-h (Garcia-Lora A et al., J Cell Physiol 2003; 195:346 55.; Kim R et al., Cancer 2004; 100:2281 91.). Therefore, mobilizing NK cells is important to increase the capacity of the host to limit the development of malignant tumors while adaptive immunity is at the states of "anergy" or "tolerance".

Macrophages and neutrophils both can be regarded as heroes and villains on tumor development. These cells are capable of phagocytosis of and antibody-dependent cellular cytotoxicity (ADCC) towards tumor cells, and secretion of tumor-growth inhibitory cytokines (Marek Jakóbisiak et al., Immunology Letters Dec. 15, 2003 pp: 103-122).

Potent biological response modifier (BRM) is manifested by stimulation of different arms of the immune system such as NK, Macrophage, lymphocytes (T and B cells).

According to Claire Lewis et al., stated in American Journal of Pathology. 2005; 167:627-635., the presence of multiple areas of hypoxia (low oxygen tension) is a hallmark feature of human and experimental tumors. Monocytes are continually recruited into tumors, differentiate into tumor-associated macrophages (TAMs), and then accumulate in these hypoxic areas. A number of recent studies have shown that macrophages respond to the levels of hypoxia found in tumors by up-regulating such transcription factors as hypoxia-inducible factors 1 and 2, which in turn activate a broad array of mitogenic, proinvasive, proangiogenic, and prometastatic genes. This could explain why high numbers of TAMs correlate with poor prognosis in various forms of cancer. In this review, we assess the evidence for hypoxia activating a distinct, protumor phenotype in macrophages and the possible effect of this on the growth, invasion, angiogenesis, and immune evasion of tumors.

Lung cancer is one of the leading causes of cancer death in the world. Non-small lung carcinoma (NSCLC) accounts for approximately 75 85% of lung cancers. Despite improvements in early detection and treatment of NSCLC in the past two decades, some patients are plagued by rapid disease recurrences and progression, and there has been no significant improvement in overall survival for such cases.

Recently, herbal therapies have increasingly been considered viable alternative treatments for malignancies (Eisenberg D M, et al., Jama 1998; 280(18):1569-1575.; Risberg T, et al., J Clin Oncol 1998; 16(1):6-12.). Of these therapies, medicinal mushrooms have a long history of use in folk medicine worldwide and in Asia Ganoderma tsugae (G. tsugae), a basidiomycetes mushroom, is one of the most popular chemopreventive mushrooms. Many bioactive components have been identified from the different parts of this mushroom, including the fruiting body, mycelia, spores and culture media.

Two major categories of bioactive ingredients are polysaccharides and triterpenes. G. lucidum has polysaccharides which, through an immune-modulatory mechanism, have in vitro and in vivo anticancer effects (Wang S Y, et al., Int J Cancer 1997; 70(6):699-705.). Some researchers have reported that triterpenes generally possess antioxidation (Zhu M, Chang Q, et al., Phytother Res 1999; 13(6):529-531.), hepatoprotection (Kim D H, et al., Biol Pharm Bull 1999; 22(2):162-164.) and anti-hypertension (Kabir Y, et al., J Nutr Sci Vitaminol (Tokyo) 1988; 34(4):433-438.) bioactivity. Recently, cytotoxic activity against tumor cells was reported from Ganoderma spp. One Ganoderma tsugae triterpene was found to induce cell apoptosis and cell cycle arrest in human hepatoma Hep3B cells, but the molecular mechanism was not investigated (Gan K H, et al., J Nat Prod 1998; 61(4):485-487).

Telomerase is a cellular reverse transcriptase that catalyzes the synthesis and extension of telomeric DNA (Greider C W, et al., Nature 1989; 337(6205):331-337.). This enzyme is specifically activated in most malignant tumors but is usually inactive in normal somatic cells, with the result that telomeres are progressively shortened during cell division in normal cells (Kim N W, et al., Science 1994; 266(5193):2011-2015.). Cells require a mechanism to maintain telomere stability to overcome replicative senescence, and telomerase activation may therefore be a rate-limiting or critical step in cellular immortalization and oncogenesis (Harley C B, et al., Curr Opin Genet Dev 1995; 5(2):249-255.), as more than 90% of human cancer cells in vivo show the presence of telomerase activity. As a ribonucleoprotein complex, telomerase in humans consists of two major subunits. These are the RNA template and the reverse transcriptase subunit, encoded by hTR and hTERT genes, respectively. Interestingly, lung cancer patients without telomerase activity survive for a significantly better prognosis than those with telomerase activity (Wu T C, et al., Lung Cancer 2003; 41(2):163-169.). This suggests that telomerase activity is an important prognostic factor in lung cancer patients.

Knowledge gained from the study of hTERT transcriptional regulation may help in designing therapies directed at suppressing hTERT transcription, and thereby the telomerase activity, in cancer cells. For example, therapies could be designed around any of the following pieces; inhibiton of the EGF receptor or HER2/Neu leads to the suppression of hTERT transcription (Budiyanto A, et al., *J Invest Dermatol* 2003; 121(5):1088-1094.; Goueli B S, et al., *Mol Cell Biol* 2004; 24(1):25-35.), most likely by abrogating the activation of the transcription factor ER81; hTERT promoter activity is inhibited through VDR upon treatment with 1K,25-dihydroxyvitamin D3 and 9-cis-retinoic acid (Ikeda N, et al., *Mol Cancer Ther* 2003; 2(8):739-746.); and the ER antagonist, raloxifene, induces a cell type-specific repression of hTERT expression (Kawagoe J, et al., *J Biol Chem* 2003; 278(44): 43363-43372.). Together these findings validate the view that in cases of cancer inhibition of telomerase function may constitute a powerful new strategy for chemoprevention and antineoplastic therapy.

SUMMARY OF THE INVENTION

The present invention is directed to an isolated and/or purified polypeptide variant or fragment of a fungal immunomodulatory protein for use in immunotherapy, treating or preventing cancer due to metastasis or suppression of telomerase activity by down-regulation of the telomerase catalytic subunit (hTERT), or activating natural killer cells, macrophage, increasing serum antibody, comprising the amino acid sequence of SEQ ID No:1

The present invention is further directed to a composition for use in immunotherapy comprising the fungal immunomodulatory protein of the present invention.

The present invention is further directed to a method for use in immunotherapy in a patient in need of such treatment, comprising administering to said patient an effective amount of the polypeptide variant or fragment of the present invention.

The present invention is also directed to a method of inhibiting or preventing growth or replication of cells of pre-existing cancer due to metastasis or suppression of telomerase activity by down-regulation of the telomerase catalytic subunit (hTERT) in a patient in need of such treatment comprising administering said patient with an effective amount of the polypeptide variant or fragment of the present invention.

The present invention is also directed to a kit for use in detecting the cancer due to metastasis or suppression of telomerase activity by down-regulation of the telomerase catalytic subunit (hTERT), comprising the fungal immunomodulatory protein according to the present invention and a detectable label wherein the protein is conjugated with or linked to the label.

BRIEF DESCRIPTIONS OF THE DRAWINGS

FIG. 1 discloses the morphological change of A549 cells treated with FIP-gts. A549 cells were treated with different concentrations of FIP-gts (0, 1, 2, 4 and 10 µg/ml) at different durations (6, 12, 24 and 72 hrs).

Figure 2:
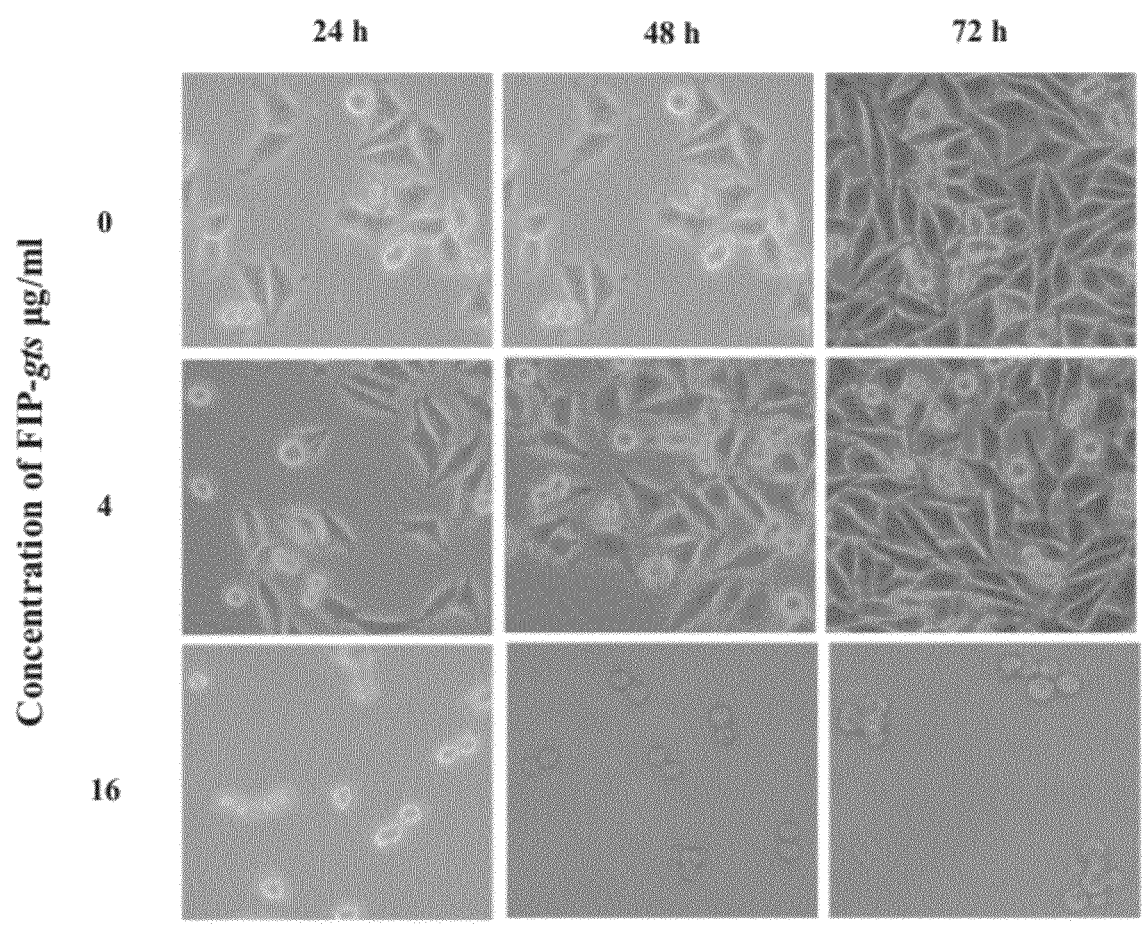

FIG. 2 discloses the morphology changes of human melanoma cancer cell line A375 after they were treated with FIP-gts. Cells were treated with 0, 4 and 16 µg/ml FIP-gts for 0, 24 and 48 hours and photographed with a phase-contrast microscope (×100).

Figure 3:
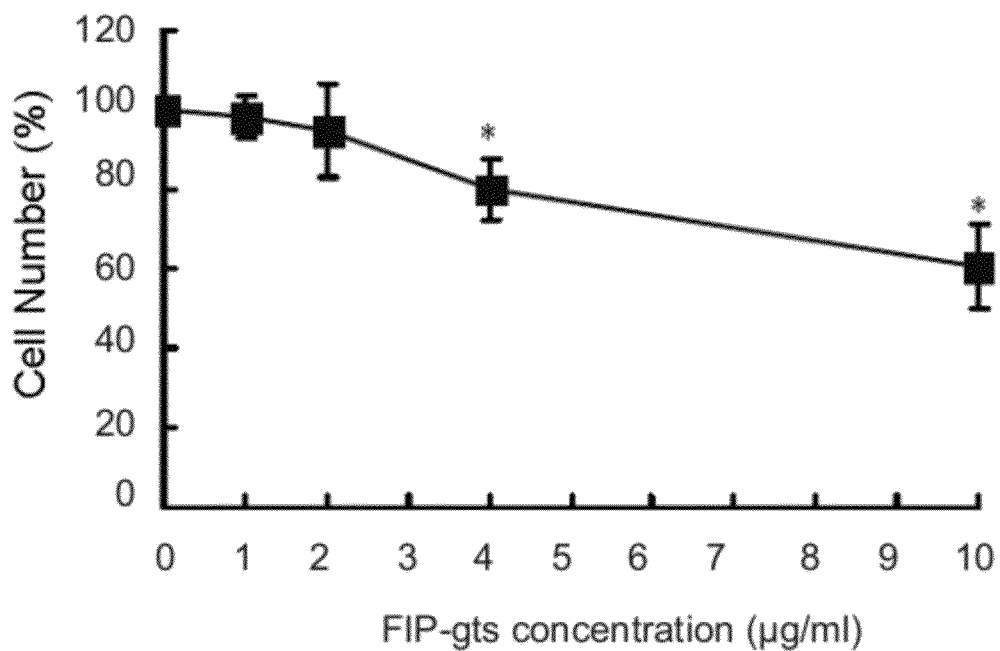

FIG. 3 discloses the growth rate of A549 cells treated with FIP-gts at different times. A549 cells were treated with 0, 1, 2, 4 and 10 µg/ml FIP-gts and viable cell numbers were measured using trypan blue dye exclusion method at 48 hrs. The data shown here are mean±standard deviation of triplicate experiments (significance calculated using student T test, *p<0.05).

Figure 4:
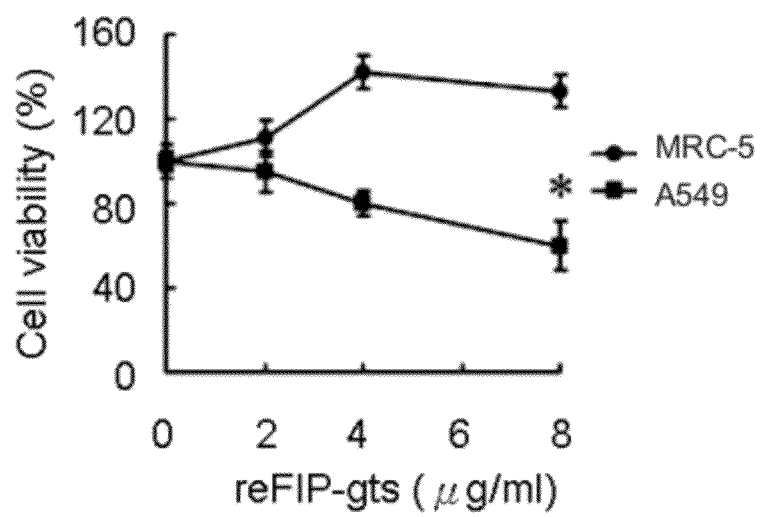
Figure 4:
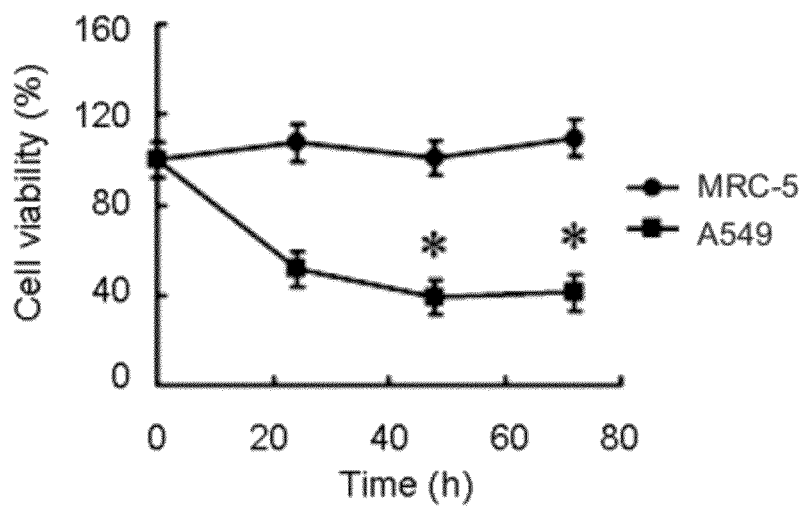

FIG. 4 shows effect of reFIP-gts treatment on A549 and MRC-5 cell viability. A549 and MRC-5 cells were treated with various concentrations of reFIP-gts (0, 2, 4 and 8 µg/ml, FIG. 4A) for 48 h and with 8 µg/ml for various time periods (0, 24, 48 and 72 h, FIG. 4B) followed by MTS assay to estimate the cell viability. The data are presented as mean±SD of triplicate experiments. The symbol (*) indicates a P<0.05 with student t test, as compared with untreated cells.

Figure 5:
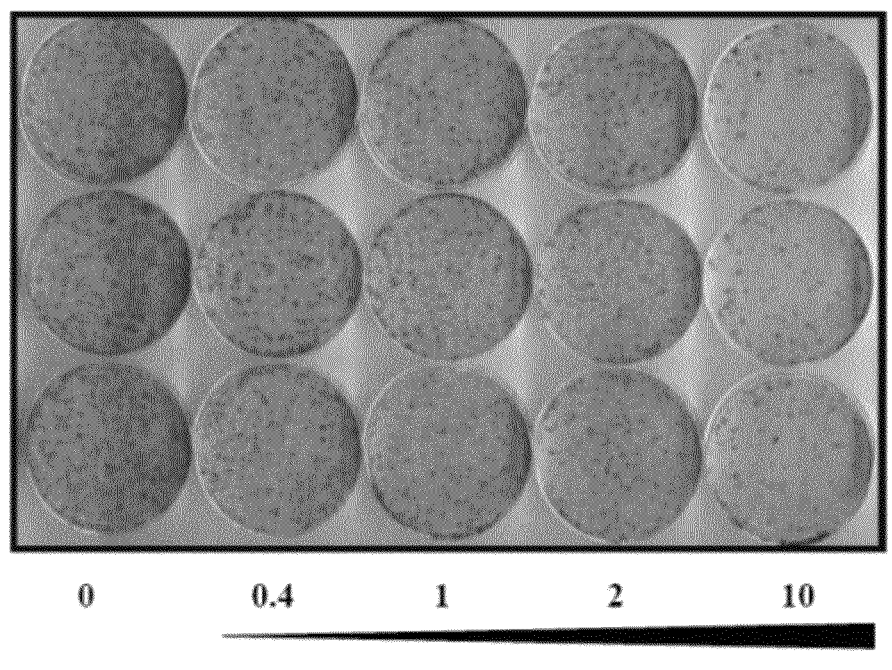
Figure 5:
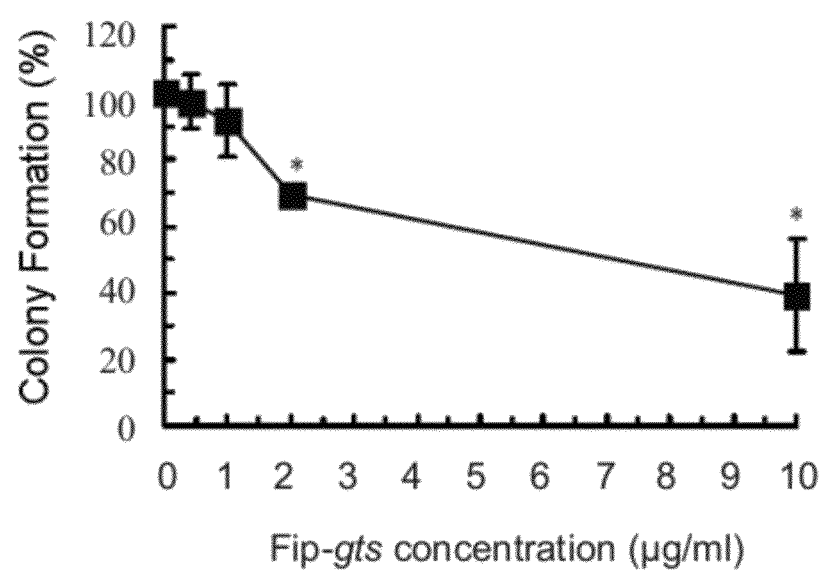

FIG. 5 shows the effect of FIP-gts on the colony formation of A549 cells. (A) Anchorage-independent growth of A549 cells treated with 0, 0.4, 1 and 2 µg/ml FIP-gts was assessed by the colony formation assay. (B) The colony number was counted under a dissection microscope. The number of cells has to be greater than 50 cells per colony. The data shown here are mean±standard deviation of triplicate experiments (significance calculated using student T test, *p<0.05).

Figure 6:
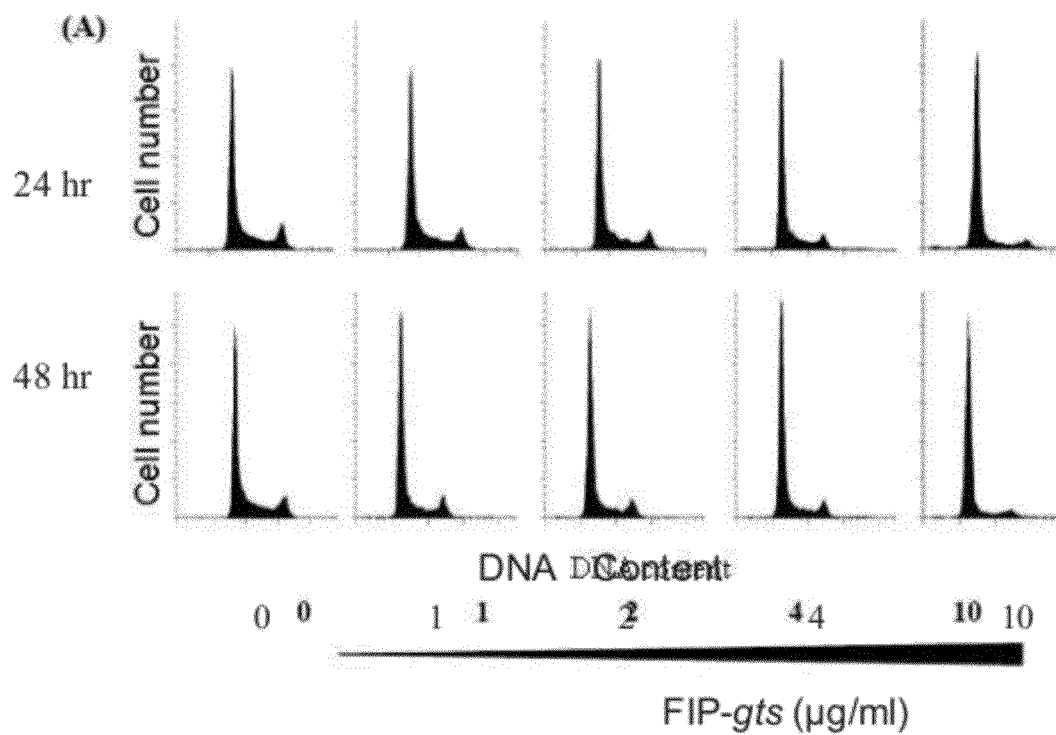

FIG. 6 shows the stage of A549 cells in cell cycle treated with different doses and time courses of FIP-gts. Cells were resuspended in 10% DMEM medium at 2×10$^6$ cells/ml. (A) Cells were detected by Flow cytometer and acquired by Cellquest. (B) Acquisition were analyzed and quantified by ModFit LT 3.0. The data shown here are mean±standard deviation of triplicate experiments (significance calculated using student T test, *p<0.05).

Figure 7:
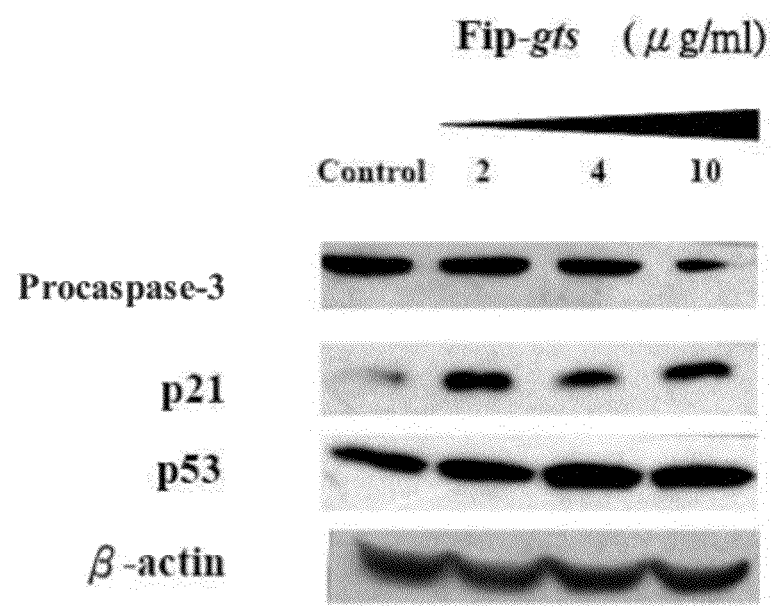

FIG. 7 shows the expression of, p21 and procaspase-3 of A549 cells treated with 0, 2, 4 and 10 µg/ml FIP-gts, respectively. Cell lysates were collected at 48 hrs and expression were determined by Western blot analysis.

Figure 8:
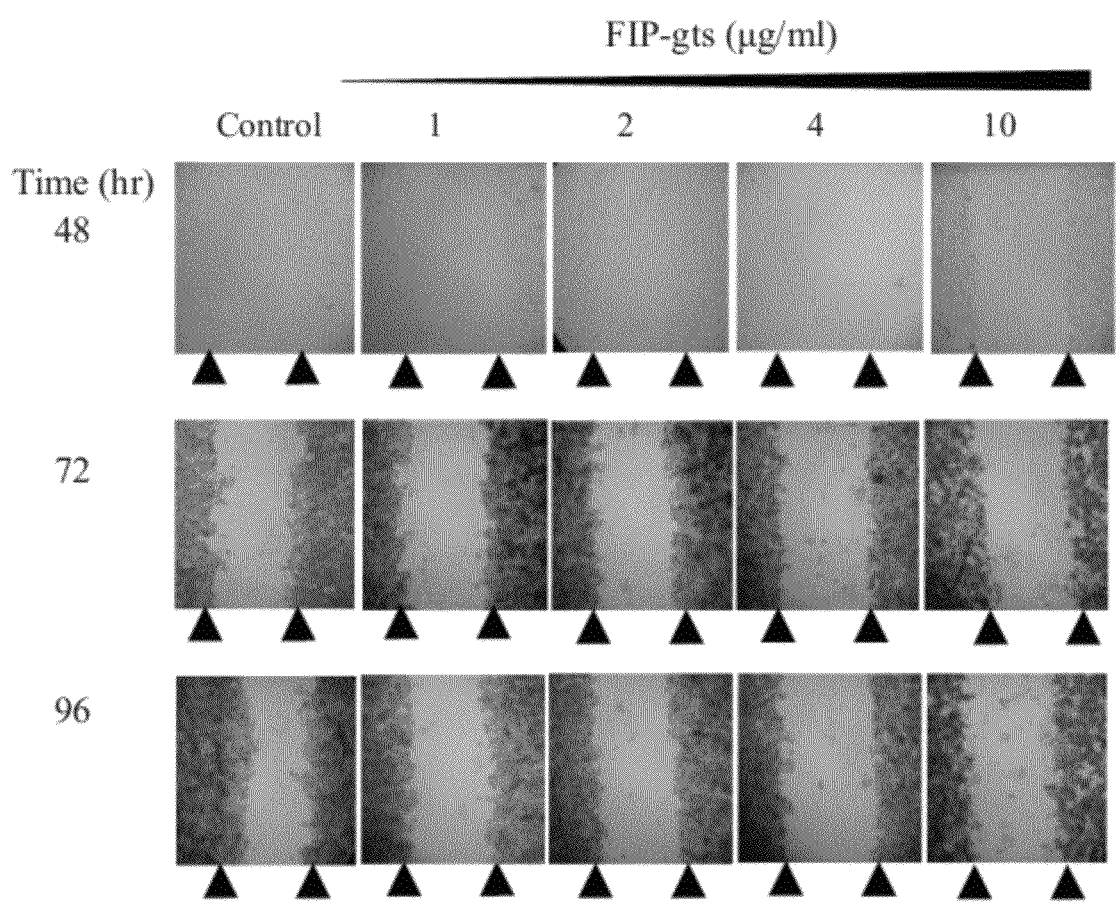

FIG. 8 shows the migration of A549 cell treated with FIP-gts into the wound. Wounds were made by scarifying confluent A549 cells by a pipette tip (arrowheads show the size of the initial wound). After incubation for 72 h or 96 h cells were fixed and stained by Geimsa stain.

Figure 9:
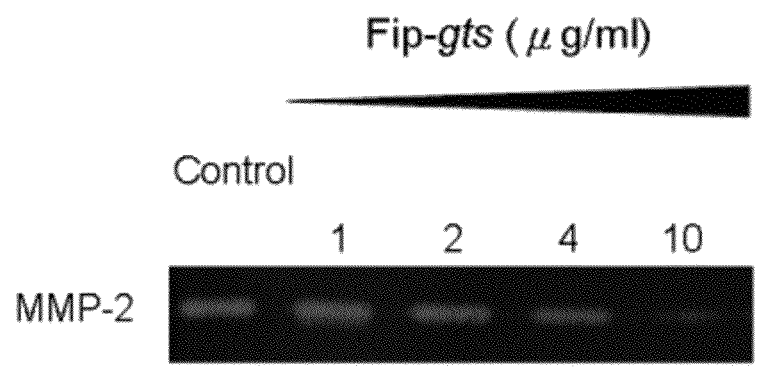
Figure 9:
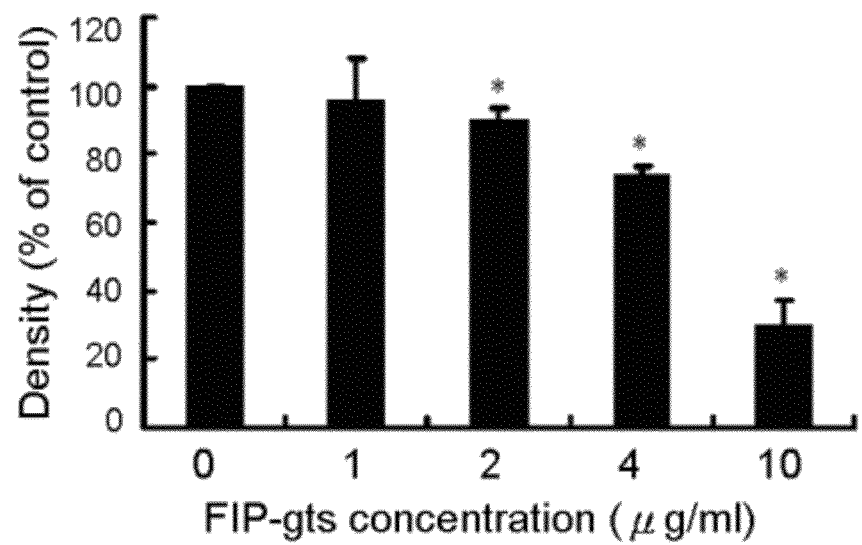

FIG. 9 shows the activity of MMP-2 treated with FIP-gts. (A) A549 cells were treated with 0, 1, 2, 4 and 10 µg/ml FIP-gts for 24 hrs. The conditioned media were collected and MMP-2 activity was determined by gelatin zymography. (B) The activity of MMP-2 was quantified by densitomertic analysis. The densitomertic data shown here are mean±standard deviation of triplicate experiments (significance calculated using student T test, *p<0.05).

Figure 10:
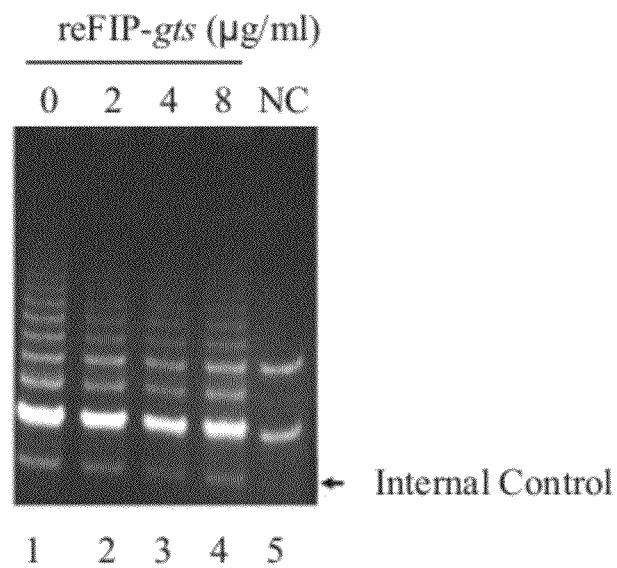
Figure 10:
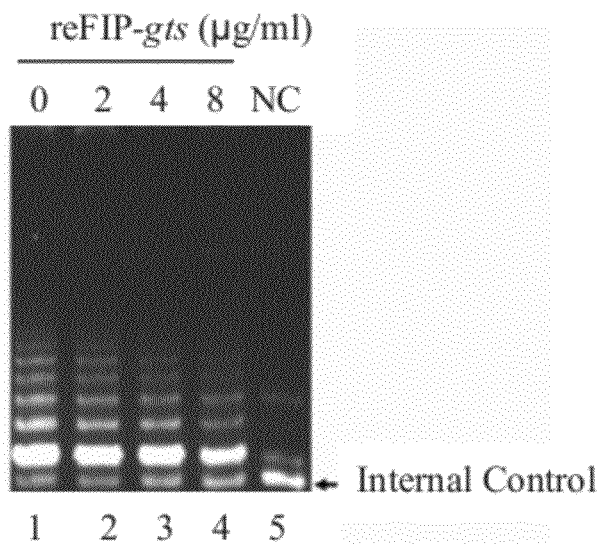

FIG. 10 shows effect of reFIP-gts on telomerase activity in A549 cells. A549 cells were treated with varying concentrations (0, 2, 4 and 8 µg/ml) of reFIP-gts (lanes 1-4, respectively) for 24 h (FIG. 10A) and 48 h (FIG. 10B). Telomerase activity in each sample was detected on TRAP assay as described in "Materials and methods." The 36-base pair internal standard was used as control. The data are representative of three independent experiments. NC (negative control, lane 5): no telomerase extract was added.

Figure 11:
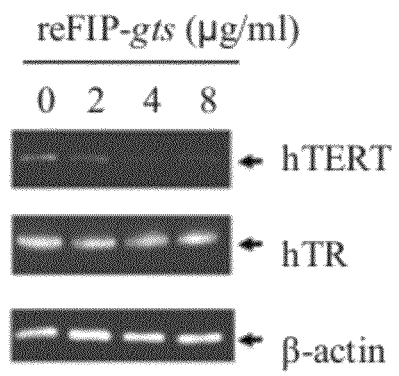
Figure 11:
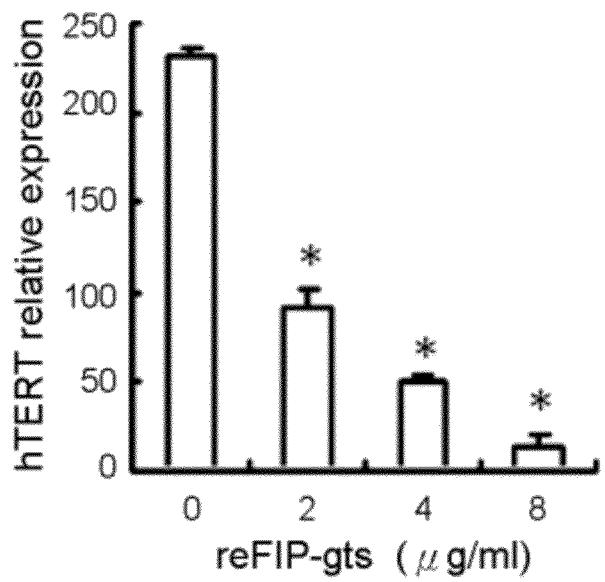

FIG. 11 shows expression of telomerase catalytic subunits at the mRNA level in reFIP-gts-treated A549 cells. Total cellular RNA from A549 cells, untreated or treated with 2, 4 or 8 µg/ml reFIP-gts for 12 h, was analyzed using (A) RT-PCR or (B) real-time PCR for hTERT, hTR and β-actin mRNA expression. Representative photographs from three independent experiments are shown. The symbol (*) indicates P<0.05 when compared with untreated cells.

Figure 12:
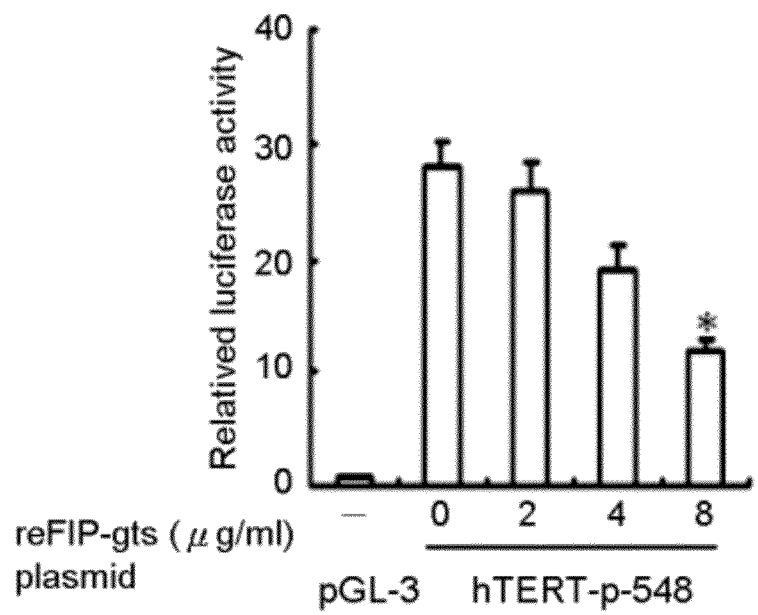

FIG. 12 shows effect of reFIP-gts on hTERT promoter activity. A549 cells were transfected with luciferase reporter plasmids containing full-length hTERT promoter (p548) and treated with 2, 4 or 8 µg/ml for 24 h, respectively. The cells were collected and luciferase assays were performed. The transcriptional activity of each reporter plasmid was normalized relative to β-galactosidase activity, and the activity in cells treated with vehicle was set at 1.0. The data are expressed as the mean fold activation ±S.E. of three transfections. The symbol (*) indicates P<0.05 when compared with untreated cells.

Figure 13:
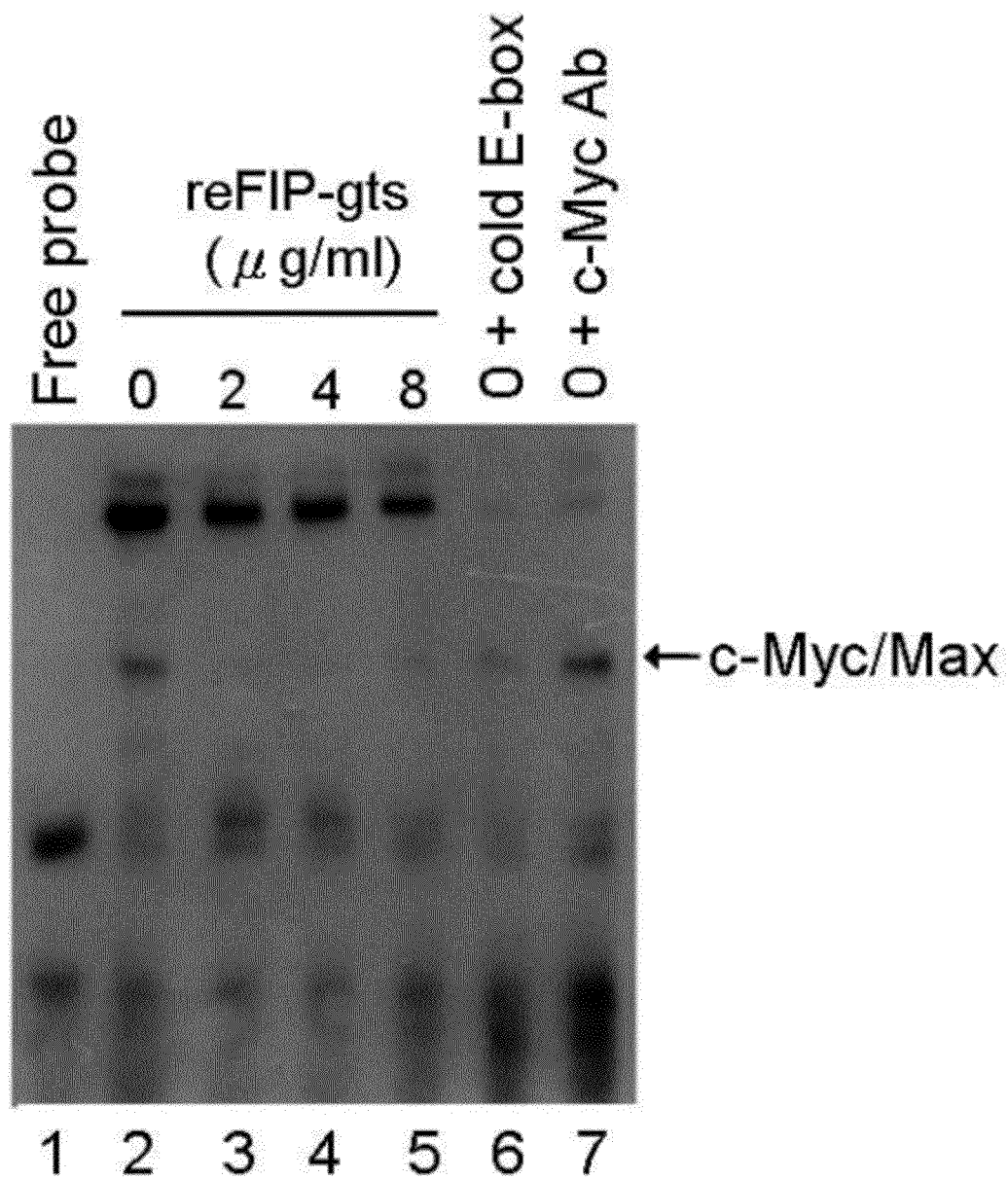

FIG. 13 shows the effects of reFIP-gts on the interaction between c-Myc and hTERT promoter in A549 cells. The presence of reFIP-gts (2, 4 or 8 μg/ml) at 48 h was detected by EMSA using nuclear extracts and biotin-labeled oligonucleotide containing the E-box DNA sequence as described in "Materials and methods." Lane 6 contains cold oligonucleotides with E-box. Lane 7 contains anti-c-Myc antibody in EMSA as described in "Materials and methods."

Figure 14:
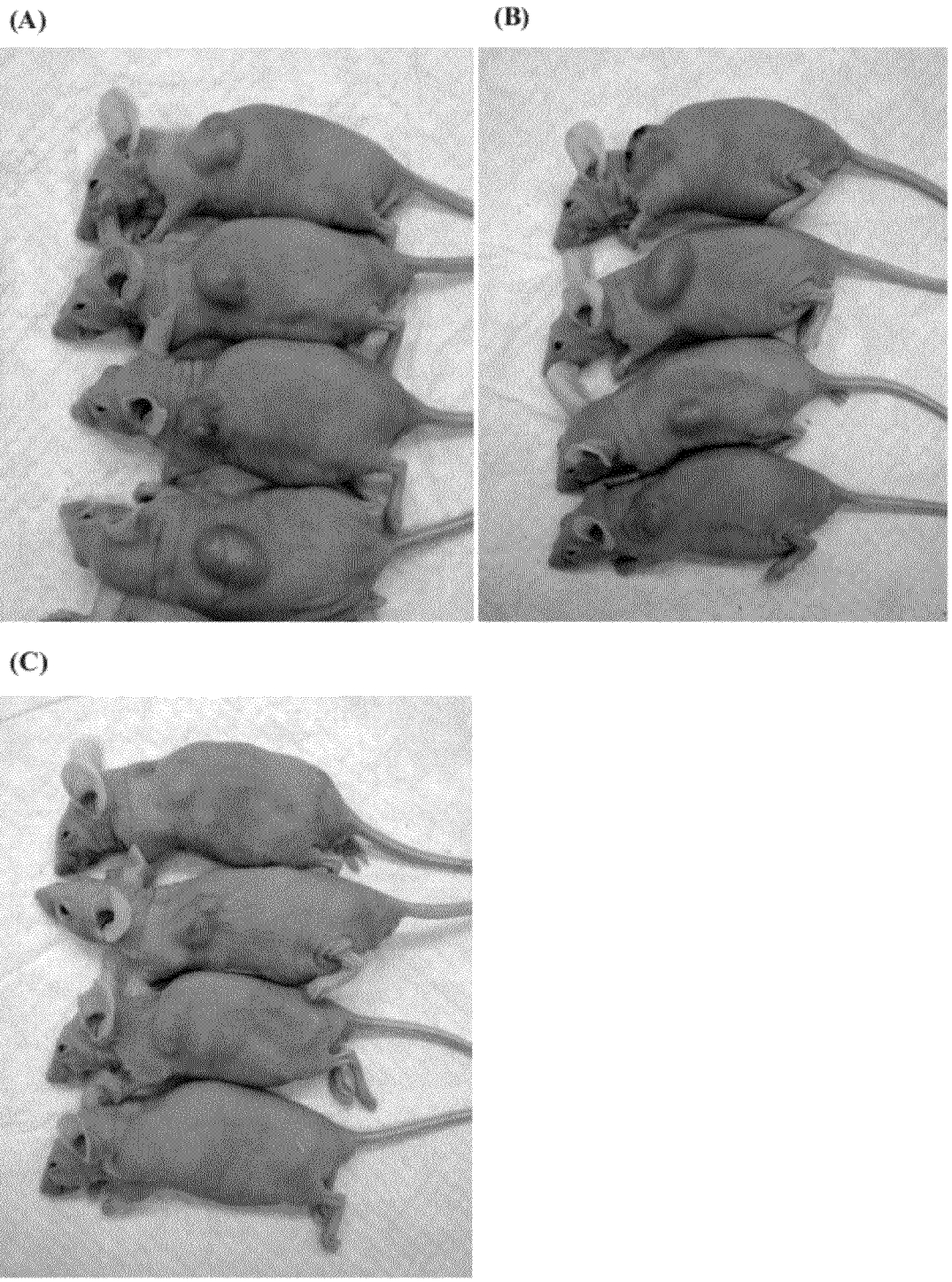

FIG. 14(a)-(c) shows the effects of FIP-gts on tumor suppression in A549 xenograft nude mice. FIG. 14 (a) shows the picture of the animals in Groups 1, which were injected i.p. with PBS each week. FIGS. 14 (a) and (b) shows the animals in Groups 2 and 3 which were injected i.p. with 8 and 32 μg FIP-gts protein each week. The pictures of all three groups were taken at 30 days after tumor inoculation.

Figure 15:
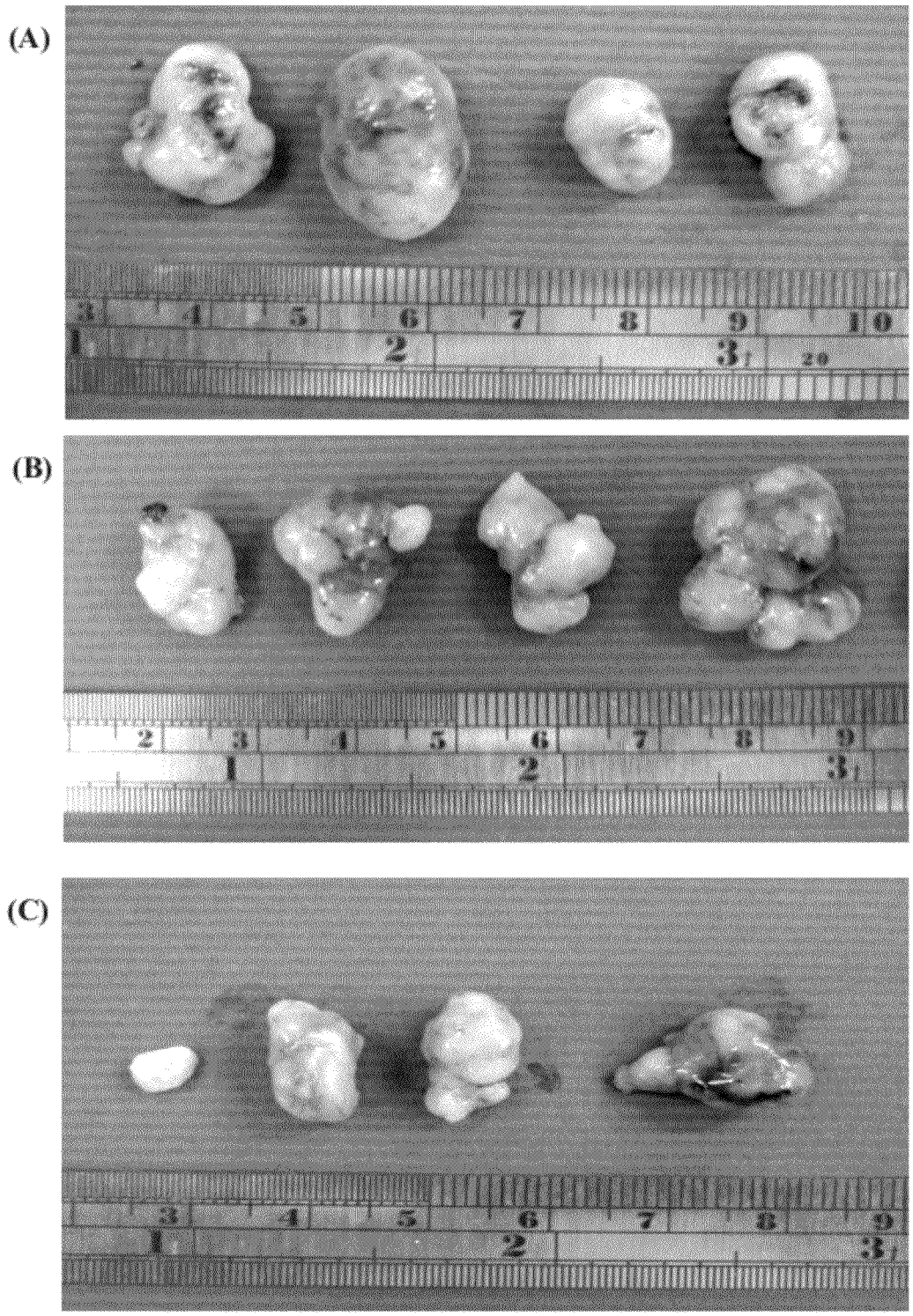

FIG. 15 shows the effects of FIP-gts on tumor suppression in vivo. FIG. 15 shows the pictures of tumors which were taken out from A549 xenograft nude mice at day 45 after tumor inoculation. FIG. 15 (a) shows the picture of tumors in Groups 1 which were treated with PBS each week. FIGS. 15 (b) and (c) shows the picture of tumors in Group 2 and 3 which were treated with FIP-gts protein at 8 and 32 μg each week.

DETAILED DESCRIPTION OF THE INVENTION

Unless defined otherwise, all technical and scientific terms used herein have the same meaning as commonly understood by one of ordinary skill in the art to which this invention belongs. Although any methods or materials similar or equivalent to those described herein can be used in the practice or testing of the present invention, the preferred methods and materials are described. For the purposes of the present invention, the following terms are defined below.

As used herein, the phrase "metastasis" or "cell invasion" refers to the ability of a cell to migrate through a physiological barrier or to protease components of an extracellular matrix. Preferred physiological barriers include basement membranes and other extracellular matrices, which are well known in the art. Cell invasion is correlated to the secretion or excretion of proteolytic enzymes from a cell. Preferred proteolytic enzymes include MMPs.

The present invention provides an isolated and/or purified polypeptide variant or fragment of a fungal immunomodulatory protein for use in immunotherapy, treating or preventing cancer due to metastasis or suppression of telomerase activity by down-regulation of the telomerase catalytic subunit (hTERT), or activating natural killer cells, macrophage, increasing serum antibody, comprising the amino acid sequence of SEQ ID No: 1

MSDTALIFRLAWDVKKLSFDYTPNWGRGNPNNFIDTVTFPKVLTDKAYTY

RVAVSGRNLGVKPSYAVESDGSQKVNFLEYNSGYGIADTNTIQVFVVDPD

TNNDFIIAQWN

The fungal immunomodulatory protein of the present invention could be obtained from *Ganoderma* species, *Volvariella volvacea* or a recombinant microorganism (such as recombinant *Escherichia coli* or Yeast).

The fungal immunomodulatory protein of the present invention could be applied as adjuvant for alleviating the pain or side effects of a patient suffering cancer.

It has been found that FIP-gts of the present invention, of which cDNA sequence is identical to LZ-8 (SEQ ID NO: 1), exhibited anti-cancer effect. It was also disclosed that cancer cells treated with FIP-gts showed reduced viability, demonstrating the utility of FIP-gts as an anticancer agent.

It has been further found that cancer cells treated with FIP-gts of the present invention exhibited a higher percentage of cells arrested at G1 phase. The G1 arrest was discovered to be a result of increased expression of p53 and p21. Therefore the present invention has developed a method of suppressing cancer proliferation by inducing G1 arrest through FIP-gts treatment.

It has been found that cancer cells treated with FIP-gts of the present invention show a decrease of MMP-2 expression. MMP-2 is an important enzyme involved in the tumor cell metastasis. Suppression of MMP-2 is a sign of FIP-gts suppressing the tumor cell metastasis.

The fungal immunomodulatory protein of the present invention has a lot of promoting immunological activities such as treating or preventing cancer due to metastasis or suppression of telomerase activity by down-regulation of the telomerase catalytic subunit (hTERT), activating natural killer cells, macrophage and increasing serum antibody.

Accordingly, the present invention provides a composition for use in immunotherapy comprising the fungal immunomodulatory protein of the present invention.

The term "immunotherapy" is not limited but to stimulate or activate immunological function (such as activate natural killer cells and macrophages or increase production of serum IgG or IgM antibody), or the activities of treating or preventing cancer due to metastasis or suppression of telomerase activity by down-regulation of the telomerase catalytic subunit (hTERT).

According to the teaching of the present invention, the down-regulation of the telomerase catalytic subunit (hTERT) is made by c-Myc.

Cancers the fungal immunomodulatory protein of the invention could treat are selected from the group consisting of lung cancer, bone cancer, breast cancer, hepatocellular carcinomas, non-small lung cell cancer, ovarian cancer and gastrointestinal cancer.

The present invention also provides a composition for use in treating or preventing cancer due to metastasis or suppression of telomerase activity by down-regulation of the telomerase catalytic subunit (hTERT), comprising the fungal immunomodulatory protein of the invention and anti-cancer compound wherein the protein is conjugated with the compound. The down-regulation of the telomerase catalytic subunit (hTERT) herein is abrogated by c-Myc binding E-box interaction.

FIP-gts conjugated with an agent (such as chemotherapeutic agents), whereas the agent may be synergistic effect on tumor cells (such as cisplatin) or is able to activate a prodrug or cytokine Thus the FIP-gts targets the agent to the metastatic tumor cells and the agent initiates destroys or decomposes the tumor cells.

In another embodiment, the FIP-gts according to the invention could be fused to an antitumor agent or a detectable label. This allows the FIP-gts to target the agent or detectable label to the tumor cells and hence allows damage/destruction or detection of the tumor. Thus, the FIP-gts is suitable for use in a method of treatment of the human or animal body by chemotherapy or surgery (e.g. radioimmunoguided surgery, RIGS), or in a method of diagnosis practiced on the human or animal body. In particular, the FIP-gts is suitable for use in treatment by surgery or therapy of a tumor, or in diagnosis of a tumor.

The antitumor agent linked to the FIP-gts may be any agent that destroys or damages a tumor to which the FIP-gts has bound or in the environment of the cell to which the FIP-gts has bound. For example, the antitumor agent may be a toxic agent such as a chemotherapeutic agent or a radioisotope, an enzyme that activates a prodrug or a cytokine.

Suitable chemotherapeutic agents are known to those skilled in the art and include anthracyclines (e.g. daunomycin and doxorubicin), methotrexate, vindesine, neocarzinostatin, cis-platinum, chlorambucil, cytosine arabinoside, 5-fluorouridine, melphalan, ricin and calicheamicin.

Suitable radioisotopes for use as anti-virus agents are also known to those skilled in the art.

The antitumor agent that is attached to the FIP-gts may also be an enzyme that activates a prodrug. This allows activation of an inactive prodrug to its active, cytotoxic form at the directed site. In clinical practice, the FIP-gts-enzyme conjugate can be administered to the patient and allowed to localize in the region of the tumor to be treated. The prodrug is then administered to the patient so that conversion to the cytotoxic drug is localized in the region of the tumor cells to be treated under the influence of the localized enzyme.

Accordingly, the present invention also provides a method for use in immunotherapy in a patient in need of such treatment, comprising administering to said patient an effective amount of the polypeptide variant or fragment of the present invention.

The present invention also provides a method of inhibiting or preventing growth or replication of cells of pre-existing cancer due to metastasis or suppression of telomerase activity by down-regulation of the telomerase catalytic subunit (hTERT) in a patient in need of such treatment comprising administering said patient with an effective amount of the polypeptide variant or fragment of the present invention.

The down-regulation of the telomerase catalytic subunit (hTERT) herein is abrogated by c-Myc binding E-box interaction.

The present invention further provides a kit for use in detecting the cancer due to metastasis or suppression of telomerase activity by down-regulation of the telomerase catalytic subunit (hTERT), comprising the fungal immunomodulatory protein of the invention and a detectable label wherein the protein is conjugated with or linked to the label to form a fluorescent protein which illuminates green or red.

The detectable label attached to the FIP-gts may be an imaging agent for site imaging such as a short-lived radioisotope, for example $^{111}$In, $^{125}$I or $^{99}$mTc.

The FIP-gts according to the invention containing a detectable label is useful for RIGS in addition to being useful for diagnosis. RIGS comprises administering a labeled protein to a patient and thereafter surgically removing any tissue to which the protein binds. Thus, the labeled FIP-gts guides the surgeon towards tissue.

In general, fungal immunomodulatory proteins are mitogenic in vitro for human peripheral blood lymphocytes (hPBLs) and mouse splenocytes. However, FIPs anticancer efficiency has not previously been well researched. The present invention has demonstrated that reFIP-gts inhibits telomerase activity via transcriptional regulation of hTERT, and provided a mechanism. That is, the binding capacity of c-Myc by reFIP-gts is inhibited, leading to telomerase activity inhibition.

At present, telomerase inhibition research focuses on (1) direct targeting of core telomerase components (Kondo S, et al., *Oncogene* 1998; 16(25):3323-3330.; Hahn W C, et al., *Nat Med* 1999; 5(10):1164-1170.); (2) telomere targeting (Rezler E M, et al., *Curr Opin Pharmacol* 2002; 2(4):415-423.; Zhang R G, et al., *Cell Res* 2002; 12(1):55-62.); (3) natural compounds and small molecules as telomerase inhibitors (Lyu S Y, et al., *Arch Pharm Res* 2002; 25(1):93-101.; Naasani I, et al., *Biochem Biophys Res Commun* 1998; 249 (2):391-396.) and (4) interference with regulatory mechanisms of telomerase (Kawagoe J, et al., *J Biol Chem* 2003; 278(44):43363-43372.).

It would be of great benefit if future research could clarify a telomerase-mediated growth inhibition mechanism. Further, A 549 cells stably expressing ectopic hTERT could be tested for growth over time with various concentrations of re-FIP-gts.

Previous studies have demonstrated a correlation between hTERT mRNA expression and telomerase activity in several cell lines and tissues. Moreover, in human cancer cells induced by various agents, the pattern of repression of telomerase activity is associated with decreased hTERT mRNA expression (Kawagoe J, et al., *J Biol Chem* 2003; 278(44): 43363-43372.; Hung C H, et al., *Gene* 1993; 127(2):215-219.; Falchetti M L, et al., *Nucleic Acids Res* 1998; 26(3): 862-863.). The present invention has demonstrated a decline in hTERT mRNA expression (FIGS. 11 and 12) to explain the inhibition of telomerase activity by reFIP-gts and the role for post-transcriptional factors in the control of telomerase function.

The regulation of hTERT promoter has been established as one of the main mechanisms in the control of hTERT mRNA levels, and c-Myc has been shown to directly bind to the hTERT promoter resulting in its activation (Wu K J, et al., *Nat Genet.* 1999; 21(2):220-224.). The down-regulation of hTERT promoter activity by repression of c-Myc has been demonstrated in previous studies (Ogretmen B, et al., *J Biol Chem* 2001; 276(35):32506-32514.). The ability of c-Myc to function as a transcription factor depends on its dimerization with the protein Max, and this interaction is mediated by HLHZip domains of the two proteins that enable the Myc/Max dimer to recognize the CACGTG or related DNA sequences known as E-box motifs (Gunes C, et al., *Cancer Res* 2000; 60(8):2116-2121.). The present invention shows that repression of the hTERT promoter is dependent on blocking the interaction in response to reFIP-gts between E-box region of the hTERT promoter and c-Myc/Max transcription factor in A549 cells (FIG. 13).

Although Horikawa et al (Horikawa I, et al., *Cancer Res* 1999; 59(4):826-830.) have suggested that c-Myc is one of the major elements participating in hTERT core promoter regulation, there might be other direct or indirect factors in the activation of hTERT promoter since this region contains the Sp 1, and AP-2, and c-Myc binding sites of. The present invention has proved that c-Myc is a main in reFIP-gts inhibition of hTERT core promoter activity.

The present invention demonstrates reFIP-gts regulation of telomerase for the first time. Using in A549 cells, reFIP-gts appears to interfere with the binding activity between c-Myc and hTERT promoter, resulting in decreased hTERT promoter binding and reduced hTERT gene transcription. These results strongly support that reFIP-gts has an anti-proliferative function, and suggest that reFIP-gts is a potential upstream candidate for the regulation of telomerase in A549 cells.

Those skilled in the art may reasonably expect that the subjects or patients, to which these methods are directed, can be any vertebrate animals, most preferred patients are humans having cancer or at risk for cancer. Nonetheless, the utility of the methods toward any vertebrate can be determined without undue experimentation by administering the composition comprising FIP-gts to a cultured cancer cell specific to the vertebrate in question and performing a simple cellular invasion assay, heal wounded assay described in the example.

The composition comprising FIP-gts may be administered to a vertebrate by any suitable route known in the art including, for example, intravenous, subcutaneous, intratumoral, intramuscular, transdermal, intrathecal, or intracerebral. Administration can be either rapid as by injection, or over a period of time as by slow infusion or administration of a slow release formulation.

It is contemplated that the compositions comprising FIP-gts are usually employed in the form of pharmaceutical preparations. Such preparations are made in a manner well known in the pharmaceutical art. One preferred preparation utilizes a vehicle of physiological saline solution; it is contemplated that other pharmaceutically acceptable carriers such as physiological concentrations of other non-toxic salts or compounds, 5% aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion by continuous or periodic infusion.

It is also contemplated that certain formulations comprising the compositions that comprises FIP-gts are to be administered orally. Such formulations are preferably formulated with suitable carriers, excipients, lubricants, emulsifying agents, suspending agents, sweetening agents, flavor agents, preserving agents and pressed as tablet or encapsulated as solid capsule or soft capsule. Or it is contemplated that such formulations are designed as following dosage forms, either oral solution, or oral sachet, or oral pellet. Or apart from being administered orally, it is contemplated that such formulations are designed as enema, or suppository, or implant, or patch, or cream, or ointment dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic, nucleic acid and other degradation and/or substances that promote absorption such as, for example, surface active agents. Compositions may be complexed with polyethylene glycol (i.e., PEGylated), albumin or the like to help promote stability in the bloodstream.

The compositions comprising FIP-gts are administered to vertebrates in an amount effective to decrease the growth or metastasis of a tumor within the vertebrate. The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein, i.e., the gelatin-zymography assay. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration. Dose administration can be repeated depending upon the pharmacokinetic parameters of the dosage formulation and the route of administration used.

The compositions comprising FIP-gts are fed to BALB/c mice to examine the effect on natural killer activity, macrophage activity and serum antibody production. As compared with various dosage groups, it demonstrates that FIP-gts promotes the activities of natural killer cells, macrophage activity and serum antibody production.

The following examples are included in the specification to help illustrate the invention and are not meant to limit the scope of the invention.

EXAMPLES

Example 1

Changes of Cell Morphology

Human pulmonary epithelial cancer cell A549 was a highly vicious pulmonary cancer cell line with high migratory capability. A549 cells as the model system was applied to examine the effect of treating or preventing cancer cells with FIP-gts.

First, the change of cell morphology after cells were treated with FIP-gts under the microscope. A549 Cells were treated with 0, 1, 2, 4 and 10 μg/ml FIP-gts, respectively, and photographed at different time interval (FIG. 1).

It was found that after cells were treated with 2, 4 and 10 μg/ml FIP-gts, the morphology of cells clearly changed at 6 hours. Cells transformed from adhering with little tentacles to round and loosely-attached cells. Some cells showed signs of moving when the culture dish was shaked. After treated with FIP-gts for 72 hours, A549 cells not treated or treated with low concentrations of FIP-gts expanded and covered the whole culture dish, whereas cells treated with high concentrations of FIP-gts showed round shape and left many spaces uncovered (FIG. 2). Normal lung cell line BEAS-2B cells treated with 0, 2, 4 and 10 μg/ml FIP-gts did not show morphology changes. And cells treated or not treated with FIP-gts exhibited similar growth rate in 24 hours, filling the culture dish almost concurrently. The control, BEAS 2B cell, were not affected by FIP-gts and filled the whole culture dish in 24 hours.

Using human melanoma cancer cell line A375, it has been found that A375 cells treated with FIP-gts seemed to lose cell-to-cell adhesion, as cells were no longer closely attached to each other but widely dispersed (FIG. 2). A375 cells were treated with FIP-gts 0, 4 and 16 μg/ml and observed after 24, 48 and 72 hours. It has been found that more cells changed to round shape when higher concentrations of FIP-gts were used (FIG. 2). It was shown that 16 μg/ml of FIP-gts could significantly inhibit cell adhesion and cell growth. Given the above, it proved that FIP-gts changed cell migratory and adhesion capability by rearranging the cell frame.

Example 2

Cell Viability Assay

Trypan blue was used to examine cell viability. The same concentration of FIP-gts in Example 1 was used to treat A549 cells. After treating cells with FIP-gts for 48 hours, trypan blue was added. Live cells could repel the trypan blue; therefore, the number of viable cells was measured by the number of cells not labeled by trypan blue.

$2 \times 10^5$ human lung epidermoid carcinoma cell line H1355 and A549 cells were inoculated to 6 cm culture dishes. H1355 cell line was a common cellular model for studying metastasis. Cells were grown at 37° C. for 16 hours. Medium was removed and FIP-gts at the concentrations of 0, 2, 4 and 10 µg/ml were treated.

Cells were collected at 48 hours after FIP-gts treatment. Cells were collected by removing the old culture medium into 15 ml centrifuge tube. Cells were washed with 1×PBS twice. Cells were resuspended in 0.5 ml TE buffer after centrifugation at room temperature for 1 min. The solution was neutralized by adding the original culture medium. Cells were transferred to a 15 ml centrifugation tube, and centrifuged at 800 rpm for 5 min. Supernatant was then discarded and cells were dispersed with 0.5 ml 1×PBS. 20 µl of cell culture was added with 5 µl Trypan blue solution. Cell numbers were counted with cell counters.

The survival rate of cells treated with 0 µg/ml FIP-gts for 48 hours was considered 100%, and the survival rate of cells treated with 1, 2, 4 and 10 µg/ml FIP-gts for 48 hours were 98.2%, 94.8%, 80.0% and 60.3%, respectively (FIG. 3). The result was consistent with the observation of the MTS assay (described below). These two experiments demonstrated that FIP-gts had cytotoxicity to A549 cells, and might suppress cell growth or cause the decrease of cells survival rate.

Example 3

Aqueous Non-Radioactive Cell Proliferation Assay (MTS)

5000 cells/dish H1355 and A549 cells were inoculated into 96-wells culture plate. Cells were grown at 37° C. for 16 hours. The culture medium was removed and FIP-gts 0, 2, 4 and 10 µg/ml were added, respectively, and cultured for 48 hours. MTS (2 mg/ml in DPBS (0.2 g KCl, 8 g NaCl, 0.2 g $KH_2PO_4$, 1.15 g $Na_2HPO_4$, 100 mg $MgCl_2.H_2O$, 133 mg $CaCl_2$.add dd $H_2O$ to 1 L)) and PMS were mixed together 20:1 and 20 µl of the mixture was added into every well. 10% SDS was added to the solution after cells were grown at 37° C. for 1 hr to stop the reaction. The absorption peak at 490 nm was measured using ELISA reader.

H1355 and A549 cells were each treated with 0, 1, 2, 4 and 10 µg/ml FIP-gts for 48 hours, respectively. Cell survival was measured by the MTS assay. MTS assay examined the cell viability by measuring the dehydrogenase activity.

It has been found that A549 and H1355 exhibited the same sensitivity to FIP-gts after treated with FIP-gts for 48 hours. The survival rate decreased as the concentration of FIP-gts increased. The survival rate of cells treated with 0 µg/ml FIP-gts for 48 hours was considered 100%, and the survival rate of A549 cells treated with 1, 2, 4 and 10 µg/ml FIP-gts for 48 hours were 79.7%, 77.9%, 72.2% and 55.2%, respectively. The survival rates of H1355 treated with the same concentrations were 79.1%, 75.3%, 71.0% and 58.2%, respectively (FIG. 4). The decrease of the cell survival rate demonstrated that FIP-gts can inhibit cell growth 50~58%.

From the MTS assay and the cell counting experiment, it demonstrated that FIP-gts showed cytotoxicity and decreased the survival rate of cancer cells.

Example 4

Counting Cell Numbers—Colony Formation

The purpose of the present experiment was to examine the cytotoxicity of FIP-gts by colony formation assay. A549 or A375 cells were treated with 0, 0.4, 2 and 10 µg/ml FIP-gts for 24 hours. And then 400 cells/60 mm dishes were grown for 12 days.

$2 \times 10^5$ A549 or A375 cells were inoculated into 60 mm culture dish. Cells were grown at 37° C. for 16 hr. FIP-gts at the concentrations of 0.4, 1, 2 and 10 µg/ml were treated to A549 cells (FIG. 5). After growing for 24 hours and washing with 1×PBS twice, cells were subcultured to new plates. 1 ml TE buffer was added and culture was let aside at 37° C. for 1 min to distach the cell. Cell numbers were counted and series cell dilution was performed with the original culture medium. 400 cells/plate cells were inoculated into 6 cm culture plates. Cells were grown in 37° C. incubators for 12 days. Cells were washed with 1×PBS twice and 0° C., 95% ethanol 2 ml was added into each plate. Culture was let aside at room temperature for 20 min. Ethanol was then discarded and 2 ml/plate 10% Geimsa stain (Geimsa stain diluted with dd$H_2O$) was added to each plate. Reaction was let aside at room temperature for 30 min. Dye was recollected and the remaining dye was gently washed out with tap water. Colony numbers were measured after dry.

The survival rate of A549 cells treated with 0 µg/ml FIP-gts was considered 100%, and the survival rate of cells treated with 0.4, 1, 2 and 10 µg/ml FIP-gts were 97.3%, 91.5%, 69.6% and 39.0%, respectively (FIG. 5A, 5B). All experiment groups except cells treated with 1 µg/ml FIP-gts showed significant decrease of survival rate (analyzed by student T test, $p<0.05$). It proved that FIP-gts showed cytotoxicity to A549 cells and suppressed colony formation.

Example 5

Flow Cytometry

It has been found that cells treated with FIP-gts showed lower survival rate. The effect might be the result of growth suppression or increased apoptosis. Traditionally anti-cancer drug suppressed cancer by modulating cell cycle, particularly arrested the cell at G1 phase. Therefore it examined whether treated A549 cells with FIP-gts modulate cell cycle, and if normal cell lines and cancer cell lines were differently affected by FIP-gts.

Cells were distributed into 60 mm culture dish, $5 \times 10^5$ cells/dish with 5 ml culture medium, grown at 37° C. for 16 hours. Old culture medium was discarded and washed twice with 1×PBS. Cells were treated with different concentrations of FIP-gts (0, 2, 4 and 10 µg/ml) at different time interval (24 hours and 48 hours). Cells were collected by the following procedures:

a. Old culture medium was moved to 15 ml centrifuge tube.
    b. Cells were washed with cold 1×PBS twice.
    c. Cells were distached by treating cells with 1× Trypsin-EDTA.

d. Old culture medium was added to stop the reaction, medium was moved to 15 microcentrifuge tube.
e. Cells were centrifuged at 800 rpm for 5 min. Supernatant discarded, pellet washed with 1×PBS twice.
f. 1 ml 70% cold ethanol was slowly added to the culture. Cells were left at 4° C. overnight to stabilize.
g. Culture was centrifuged at 800 rpm for 5 min. Supernatant discarded.
h. Culture was washed with ice cold 1×PBS twice. Supernatant was discarded and let dry as much as possible.
i. 1 ml propidium iodide (PI) mixture to each tube was added to each tube (avoid light)

| | |
|---|---|
| 1XPBS | 550 µl |
| 5% Triton X-100 | 200 µl |
| 250 µg/ml propidium iodide | 200 µl |
| 0.5 mg/ml RNase A | 50 µl | j. Sample was let aside at room temperature for 30 min.
k. Culture was filtered with 40 µm nylon mesh to avoid oversized cell clusters or debris stuck the entrance hole of flow cytometer. Single cell suspension in flow cytometer tube was collected.

To measure the DNA in cells, the experiment used Fluorescence-Activated Cell Sorter (FACS) system to sort cells and analyzed with FACSCalibur (BECTON DICKINSON). The absorbance of red fluorescence at 617 nm determined the DNA content of cells labeled with PI. The measurement was analyzed by program CELL Quest. The statistics were computed and cell numbers at different stages of cell cycle were displayed using program Mod Fit 3.0.

Using flow cytometer, it has been found that cells treated with FIP-gts showed a profound arrest at G1 phase. At most more than 30% cells were found to be at G1 phase. The G1 phase arrested decreased the proportion of cells at S phase. In other words, cell growth was suppressed by FIP-gts. Fewer cells were found to be at SubG1 phase. The highest proportion of cells at subG1 phase (1.6%) were found at the second day after cells were treated with high concentrations of FIP-gts. The phenomenon suggested that FIP-gts lowered the cell curvival rate by causing G1 phase arrest and minor apoptosis.

The results showed that the higher concentrations of FIP-gts treated, the more cells arrested at the G1 phase. A549 cells treated with 0, 1, 2, 4 and 10 µg/ml FIP-gts for 24 hours showed a proportion of 58.2%, 59.1%, 62.0%, 64.0% and 75.5% cells at the G1 phase, respectively. The increase of G1 phase also caused the decrease of cells at their S phase. A549 cells treated with the same concentrations of FIP-gts as above showed a proportion of 32.8%, 30.9%, 30.1%, 27.2% and 18.2% at their S phase (FIGS. 6A and 6B), respectively. The cells arrested at G1 phase also increased as the time of FIP-gts treatment increased. A549 cells treated with the same concentrations of FIP-gts as described above for 48 hours showed a proportion of 60.2%, 68.8%, 72.6%, 76.1% and 82.1% at their G1 phase, respectively, and the same cells showed an even lower proportion of cells at their S phase, respectively 31.8%, 25.1%, 23.0%, 20.0% and 13.8%. Thus the experiment demonstrated that FIP-gts caused A549 cells to arrest at G1 phase (FIGS. 6A and 6B).

It has been found that few cells were at their SubG1 phase when A549 cells were treated with 10 µg/ml 的 FIP-gts. Moreover, fewer cells went through apoptosis when they were treated with FIP-gts. 0.9% and 1.6% of A549 cells treated with FIP-gts 10 µg/ml for 24 hours and 48 hours, respectively, were at their SubG1 phase (FIG. 6B).

Example 6

Western Blot

External signals, such as UV, cisplatin could activate and stabilize p53 protein. p53 further activated other downstream genes including p21. p21 was the major checkpoint protein of the G1 phase in cell cycle (Zhong, X. et al, 2004. *Int. J. Cancer*). Using western blot, it has been found that the expression of p53 protein was induced after treating cells with FIP-gts for 48 hours. Gene p21 was also induced, demonstrating that FIP-gts caused cells to arrest at G1 phase by activating p21.

There were three routes of apoptosis: through ER, death receptor or mitochodria. All three pathways resulted in the cleavage of procaspase 3 (32 kD) into the active caspase 3 (17 kD). Caspase 3 was the final executor of the caspase series. It led to cell apoptosis, DNA breakage, nucleus condense and the formation of inclusions (Di Pietro, R., et al. (2004) *Int J Immunopathol Pharmacol* 17 (2)181-190). It has been found that when cells were treated with high concentrations of FIP-gts, there was a slight decrease of procaspase-3, the result of cleavage of procaspase-3 into active caspase-3.

From the results of the flow cytometer it has been found that FIP-gts caused cells to arrest at G1 phase and initiate minor apoptosis at high concentrations. Therefore the change of protein expression was studied when cells were treated with FIP-gts.

a. Sample Preparation

A549 $5 \times 10^5$ cells/plate were inoculated to 60 mm culture dish. Cells were grown at 37° C. for 16 hours. Cells were treated with 0, 2, 4 and 10 µg/ml FIP-gts and grown at 37° C. incubator for 48 hours. Cells were first washed twice with PBS. Supernatant was discarded and 100 µl cell buffer (10 mM EDTA, 10 mM EGTA, 5 mM NaF, 10% glycerol, 1 mM DTT, 400 mM KCl, 0.4% Triton X-100, 20 mM sodium β-glycerophosphate, 0.1 mM $Na_3VO_4$, 1 mM PMSF/DMSO, 3 µg/ml aprotinin, 2 µg/ml pepstatin A, 2 µg/ml Leupeptin, 1× phosphatase inhibitor cocktail I (Sigma, P2850) were added; 1× phosphatase inhibitor cocktail II (Sigma, P5726)) was also added to dissolve cells. The reaction was left on ice and cells were homogenized using ultrasonice homogenizer at 4° C. two times with an interval more than 10 minutes. Cells were centrifuged again at 12000 rpm, 4° C. for 20 min. Supernatant was carefully moved to another sterilized 1.5 ml micron and the protein content was quantified. The whole process of treating FIP-gts, centrifuging cells and adding 2×SDS sample buffer (200 mM Tris pH6.8, 8% SDS, 40% Glycerol, 2.86 M 2-mercaptoethenol and appropriate amount of bromophenol blue), to heat at 95° C., must be finished in 2 hours.

b. Protein Quantification

Bio-Rad solution was applied to quantify protein concentration. First Bio-Rad reagent was diluted with dd $H_2O$ 4:1, this was the Bio-Rad protein detection reagent. The sample, the supernatant of the cell culture 2 µl and the diluted Bio-Rad protein detection reagent 498 µl was mixed. Sample was reacted in 1.5 ml micron at 37° C. for 20 min. The absorbance peak was measured by spectrophotometer at 595 nm and compared with the absorbance peak of standard sample bovine serum albumin (BSA) to get the protein quantity (µg/µl). The standard BSA quantity was measured by adding 2 µg, 4 µg, 6 µg, 8 µg and 10 µg BSA into diluted Bio-Rad protein detection reagent 498 µl, 496 µl, 494 µl, 492 µl and 490 µl, respectively. Sample was reacted in 1.5 ml micron at 37° C.

for 20 min. The sample absorbance peak at 595 nm was also measured. The BSA measurement was measured to obtain the standard correlation of protein quantity with peak absorbance. The protein quantity of the sample protein thus could be determined by putting in the peak absorbance of the sample.

c. SDS-PAGE

TABLE 1

The running gel was prepared as follows:

|  | 15% | 12.5% | 10% |
| --- | --- | --- | --- |
| dd H$_2$O | 6.3 ml | 7.6 ml | 8.8 ml |
| 1.5M Tris pH 8.8 | 5 ml | 5 ml | 5 ml |
| (38.67:1.33) Acrymide:Bis | 7.5 ml | 6.2 ml | 5 ml |
| 10% SDS | 0.2 ml | 0.2 ml | 0.2 ml |
| APS(10 mg/ml) | 1 ml | 1 ml | 1 ml |
| TEMED | 10 μl | 10 μl | 10 μl |
| Total Volume | 20 ml | 20 ml | 20 ml |

TABLE 2

The 3% stacking gel was prepared as follows:

| dd H$_2$O | 3.54 ml |
| --- | --- |
| 0.5M Tris pH 8.8 | 1.5 ml |
| (38.67:1.33) Acrymide:Bis | 0.45 ml |
| 10% SDS | 0.06 ml |
| APS(10 mg/ml) | 0.3 ml |
| TEMED | 15 μl |
| Total Volume | 6 ml |

The sample was run on SDS-PAGE, and Hybond-P membrane (Pharmacia) was prepared 20 minutes before electrophoresis finishes. The membrane was wet with methanol for 15 second, washed with ddH$_2$O for 10 min, and then the membrane was transferred to the transfer buffer (20% methanol, 192 mM Glycine, 25 mM Tris-HCl, pH 9.2) for at least 10 min. The gel was carefully taken off after electrophoresis and transferred to Hoefer Semiphor following standard protocol. The transferred-membrane was blocked in shaking TTBS buffer (50 mM Tris, 0.2% Tween 20, 150 mM NaCl, pH 7.5) with 5% nonfat milk powder for 1 hour.

d. Antibody Detection

Specific primary antibody was added to block Hybond-P membrane. 1×TTBS buffer with 3% BSA was added to dilute the following primary polyclonal antibody: anti-caspase-3 (1:500, Cayman), anti-COX-2(1:1000, Cayman #160106). 1×TTBS buffer with 5% nonfat milk powder was used to dilute the following primary antibody: anti-BAX (1:8000, R&D), p53 (1:500, DAKO), p21 (1:500, Zymed). Sample was shaken at 4° C. overnight (at least 16 hours). The membrane was taken out the other day. The membrane was washed with 100 ml 1×TTBS buffer with 3% nonfat milk powder twice, 10 min each time. Anti-rabbit IgG-HRP (1:5000, Cell Signaling #7074) or anti-mouse IgG-HRP secondary antibody (1:10000, Chemicon AP124P) was diluted with 1×TTBS buffer with 3% nonfat milk powder. Sample was shaken at room temperature for 1 hour. The washing procedure was repeated once. E.C.L. color development reagent (NEN, NEL105) was mixed 1:1 with Enhanced luminol reagent and Oxidizing reagent. The membrane was put face up into the container with color development reagent and let react for 5 min to develop the HRP color. The fluorescence was exposed on X-ray film for 3-5 min, and then developed and fixed the image.

The most important checkpoint of G1 phase was p21. It has been found that after treating with 0, 2, 4 and 10 μg/ml FIP-gts for 48 hours, p21 expression was significantly induced (FIG. 7). It was also know that p21 was activated by p53, another well-known oncogene. The western blot result also showed that the expression of p53 was induced by FIP-gts (FIG. 7). Therefore it proved that FIP-gts induced the expression of p53, increased the amount of p21 and caused G1 pause.

It has been found that procaspase-3 was decreased when cells were treated with 10 μg/ml FIP-gts (FIG. 7). Thus procaspase-3 was activated into caspase-3 when cells were treated with FIP-gts, causing cells to undergo apoptosis. Moreover, the decrease of cells was not a result of enhanced apoptosis, but the result of suppression of proliferation.

Example 7

Wound Healing Assay

Using wound healing assay, it has been found that FIP-gts could effectively suppress the mobility of breast cancer cells.

2×10$^5$ A549 cells were gown in 24 well culture dish. Cells were grown until almost cover the culture plate and cells were treated with culture medium containing 0.5% FBS for 24 hours to suppress cell growth. The plate was scarified with blue tip and cells were washed with 1×PBS. Finally different concentrations of 1, 2, 4 and 10 μg/ml FIP-gts were added. Pictures were taken every 24 hour and cell migration was monitored.

Usually cancer cells obtained mobility before they performed metastasis. Wound healing assay was applied to examine whether treating cells with 0, 2, 4 and 10 μg/ml FIP-gts would increase the mobility of cells. It has been found that when cells were treated with FIP-gts for 48 hours, no significant mobility was observed. The invention identified cell migration that covered the line when cells were treated with 0, 1 and 2 μg/ml FIP-gts for 72 hours. Cells treated with 4 and 10 μg/ml FIP-gts almost showed no sign of migration. Compared cells treated or not treated with FIP-gts for 96 hours, cells not treated with FIP-gts showed substantial mobility and covered ⅓ of the scarified line, whereas cells treated with low concentrations of FIP-gts showed some migration, and cells treated with high concentrations showed no migration (FIG. 8).

Using wound healing assay, it has been found that cell mobility were suppressed when treated with FIP-gts. When the FIP-gts treated exceeded 4 and 10 μg/ml, A549 cells showed almost no mobility.

Example 8

Gelatin Zymogragphy

During metastasis, metaloproteinase digested extracellular matrix, dissociated cells and extracellular matrix and provided cells mobility. It was known that metalloproteinases MMP-2 and MMP-9 were highly expressed in many vicious cancers (Johnsen, M., et al., Curr Opin Cell Biol, 1998. 10, 667-671). Therefore the expression of MMP-2 and MMP-9 and the metastasis of cancer cells were highly correlated (Curran, S, and Murray, G. I. Eur J Cancer, 2000. 36, 1621-1630., Liabakk, N. B., et al., Cancer Res, 1996. 56, 190-196.).

In order to avoid the interference of MMP-2 and MMP-9 in the serum, serum starvation on cell cultures and treated A549 cells with FIP-gts were applied to analyze the activity of MMP. To further improved the accuracy of gelatin zymography assay, Bio-Rad also been used to quantify protein concentration as a measure of cell density.

It has been found that cells treated with high concentrations of FIP-gts can suppress the expression of MMP-2. It also found that the effect of FIP-gts was dose-dependent.

A549 cells were grown $1 \times 10^5$ cells/well in 24 well plate. Serum-free medium 200 µl/well were added the other day and cells were treated with 0, 2, 4 and 10 µg/ml FIP-gts for 24 hours. Medium was removed and cells were washed with 1×PBS. Cells were collected with CE buffer and proteins were quantified using Bio-Rad. 2% gelatin was prepared by dissolving 2 g Gelatin/100 ml ddH$_2$O at 55° C.

TABLE 3

8% SDS-PAGE gel was prepared with 0.1% Gelatin:

|  | 8% |
|---|---|
| dd H$_2$O | 3.0 ml |
| 1.5M Tris pH 8.8 | 2.0 ml |
| (38.67:1.33) Acrymide:Bis | 2.2 ml |
| 10% SDS | 0.08 ml |
| APS (10 mg/ml) | 0.4 ml |
| 2% Gelatin | 0.4 ml |
| TEMED | 10 µl |
| Total Volume | 8 ml |

The gel was prepared as described in the western blot experiment. Gel was put in electrophoresis chamber with electrophoresis buffer. Culture media was loaded with 5× dye (0.1% SDS, 104 mM Tris-HCl pH 6.8, 50% Glycerol (or 25 g sucrose), 0.125% bromophenol blue) into the gel and perform electrophoresis. Gel was then washed with washing buffer (40 mM Tris-HCl pH 8.5, 0.2 M NaCl, 10 mM CaCl$_2$, 2.5% Triton X-100) at room temperature for 30 minutes twice, and reaction buffer (40 mM Tris-HCl pH 8.5, 0.2M NaCl, 10 mM CaCl$_2$, 0.01% NaN$_3$) was added. Let react at 37° C. incubator for 12 hours. The membrane was dyed with Coomassie blue (0.2% Coomassie blue R-250, 50% methanol, 10% acetic acid) for 30 minutes. Gel was destained with 10% acetic acid and 20% methanol. Membrane was dried in 50% ddH$_2$O, 50% methanol and 0.33% glycerol for 30 minutes. The membrane was then sealed in glass paper.

Because cell mobility is correlated to the expression of MMP, gelatin-zymograpghy was applied to analyze whether the activity of MMP-2 is altered by treating cells with FIP-gts. It has been found that the expression of MMP-2 significantly decreased when the amount of FIP-gts treated increases (student T test, *p<0.05). The expression of MMP when cells were not treated with FIP-gts was considered 100%. It has been found that the expression of MMP treated with 1, 2, 4 and 10 µg/ml were 95.7%, 90.3%, 73.6% and 29.8%, respectively (FIG. 9). Thus it concluded that FIP-gts modulates cell migratory through regulating the expression of MMP-2.

Example 9

Reverse Transcriptase Polymerase Chain Reactions, RT-PCR

Since treated cells with high concentrations of FIP-gts shortly could caused the decrease of metalloproteinases expression, RT-PCR was applied to measure the mRNA expression of TIMP-1 (Tissue inhibitor of metalloproteinases), the inhibitor of metalloproteinases, after treating cells with FIP-gts. It has been found that the mRNA expression of TIMP-1 and PAI increased when cells were treated with FIP-gts 0, 2, 4 and 10 µg/ml for 24 hours. It also found that the mRNA expression of MMP-2 decreased but the expression of TIMP-2 was not affected. Thus it concluded that treated cells with FIP-gts caused the mRNA expression of MMP-2 to decrease, and activities of other MMPs such as MMP-9 would be suppressed by the increase expression of TIMP-1. Thus the cell metastasis was inhibited by treating cells with FIP-gts.

RT-PCR was performed by using Promega RT-PCR kit as follows:

1 µg total RNA was heated at 70° C. After 10 minutes, the heated RNA was cooled in ice bath. Then, 25 mM MgCl$_2$ 4 µl, 5×MMLV buffer 4 µl, 10 mM dNTP Mixture 2 µl, Recombinant RNasin Ribonuclease inhibitor 0.5 µl, MMLV Reverse transcriptase 1 µl, Oligo (dT)$_{15}$ Primer 1 µl and Nuclease-Free Water were added until the final volume was 20 µl.

TABLE 4

Primers for performing RT-PCR:

| Enzyme | SEQ ID | Sequence 5'→3' | Position (bp) | Temp(° C.) |
|---|---|---|---|---|
| MMP-2 | SEQ ID No: 2 | 5'-GGCCCTGTCACTCCTGAGAT-3' | 1337-1356 | 62° C. |
|  | SEQ ID No: 3 | 5'-GGCATCCAGGTTATCGGGGA-3' | 2026-2007 |  |
| PAI-1 | SEQ ID No: 4 | 5'-GGATCCAGCCACTGGAAAGGCAACATG-3' | 1470-1490 | 55° C. |
|  | SEQ ID No: 5 | 5'-GGATCCGTGCCGGACCACAAAGAGGAA-3' | 1236-1216 |  |
| TIMP-1 | SEQ ID No: 6 | 5'-TGGAGAGACACTGCCAACTTG-3' | 1700-1720 | 58° C. |
|  | SEQ ID No: 7 | 5'-AGGCTGTGCCTTCCTACAGA-3' | 2224-2204 |  |

Example 10

Increased Cytokine Expression

Human peripheral blood mononuclear cells (PBMCs) were treated with 0, 1.25, 2.5, 5 and 10 µg/ml FIP-gts. After 48 hours the cytokine expression of human PBMCs was measured by ELISA. It has been found that the expression of cytokines IL-2, IFN-γ, TNF-α and IL-4 increased as the concentrations of FIP-gts treated increased (Table 5).

TABLE 5

The increased cytokine expression of human PBMCs treated with FIP-gts.

| | FIP-gts (µg/ml) | | | | |
|---|---|---|---|---|---|
|  | 0 | 1.25 | 2.5 | 5 | 10 |
| IL-2 (pg/ml) | 116 | 316 | 272 | 425 | 1218 |
| IFN-γ (pg/ml) | 70 | 4135 | 4578 | 4378 | 4372 |
| TNF-α (pg/ml) | 89 | 1174 | 2076 | 3525 | 2219 |
| IL-4 (pg/ml) | 5 | 3 | 7 | 13 | 39 |

Example 11

Comparing Effects of FIP-gts on Three Different Cell Lines

The effects of FIP-gts on 3 cancer cell lines: human prostate cancer cell line PC3, human breast cancer cell line MDA231 and human melanoma cancer cell line A375 were assessed (Table 6). The effects of FIP-gts were assessed by observing the morphology changes of cells treated with FIP-gts, following protocol described in Example 1; by measuring the inhibition of cell proliferation, following protocol described in Example 3; and by measuring the inhibition of colony formation, following the protocol described in Example 4.

TABLE 6

Effects of FIP-gts on different cancer cell lines

| Cell line | Cell line origin | Morphology change | Inhibition of cell growth | Inhibition of colony growth |
|---|---|---|---|---|
| PC3 | Human prostate cancer | n.d. | + | + |
| MDA231 | Human breast cancer | n.d. | + | + |
| A375 | Human melanoma cancer | + | + | + |

Example 12

Materials and Methods

Cell Lines and Culture

A549 human lung adenocarcinoma cells and MRC-5 human normal lung fibroblasts were obtained from the American Type Culture Collection. Both cell lines were maintained at 37° C. in a 5% $CO_2$ humidified atmosphere on Dulbecco's modified Eagle's medium (DMEM) (GIBCO) and Basal medium Eagle (BME)(Sigma) medium containing 10% fetal bovine serum (FBS; Life Technologies, Inc., Rockville, Md.) and 100 ng/ml each of penicillin and streptomycin (Life Technologies, Inc.).

Expression of reFIP-gts Fusion Protein

The FIP-gts plasmid DNA was generously provided by Dr. Jung-Yaw Lin (National Taiwan University, Taiwan). In order to obtain expression of recombinant GST-FIP-gts, recombinant plasmids were introduced into *E. coli* strain XL-10 by $CaCl_2$-mediated transformation. When the cells reached a density of $4 \times 10^8$ cells/ml, they were induced (0.5 mM isopropyl-1-thio-β-D-galactopyranoside was added) and the culture was incubated for an additional 3 h. Cells were harvested by centrifugation and resuspended in 10 ml of ice-cold resuspension buffer (with 10 mM Tris-HCl, pH7.5, 100 mM sodium chloride, 1 mM magnesium chloride, and 1 mM dithiothreitol). Cells were treated with lysozyme (0.2 mg/ml) and then lysed via three cycles of freeze/thawing. Cell lysate was cleared by centrifugation (20,000×g for 20 min), and supernatant was directly applied onto a glutathione-Sepharose 4B column (2 ml), equilibrated with 10 mM Tris-HCl, pH 8.0. The column was washed with 20 ml of equilibrium buffer and then eluted with 5 mM reduced glutathione in the equilibrium buffer to obtain the fusion protein (Kim N W, et al., *Science* 1994; 266(5193):2011-2015.). The fusion protein was treated for 48 hours at 25° C. with thrombin at an enzyme-to-substrate molar ratio of 1:100 in buffer (50 mM Tris-HCl, pH 8.0). Reaction products were applied onto a CM-52 column (20 mm×30 mm) equilibrated with Tris-HCl buffer (50 mM, pH 8.0), and then eluted with a linear gradient from 0 to 0.3 M sodium chloride in the same buffer (data not shown). Active fractions were detected in the first peak on IFN-γ stimulatory activity assay as previously described (Wang P H, et al., *J Agric Food Chem* 2004; 52(9):2721-2725.).

Cell Proliferation Assay

MTS assay was used to determine the effect of reFIP-gts on the proliferation of A549 and MRC-5 cells. In metabolically active cells, MTS β-(4,5-dimethylthiazol-2-yl)-5-(3-carboxymethoxyphenyl)-2-(4-sulfophenyl)-2H-tetrazolium) (Promega) was reduced by dehydrogenase enzyme into an aqueous, soluble formazan product. Absorbance was measured directly at 490 nm from 96-well assay plates without additional processing. The quantity of formazan was considered to be directly proportional to the number of viable cells in the culture.

Briefly, the cells ($5 \times 10^3$) were incubated on 96-well plates containing 200 μl of growth medium. After 24 h incubation, the medium was carefully removed and 100 μl of fresh medium containing various concentrations of reFIP-gts was added to the wells. The cells were treated with reFIP-gts, continuously for 48 h with 2-8 μg/ml and for various time periods with 8 μg/ml. At the end of this process, 20 μl/well of combined MTS/PMS solution was added and wells were incubated (1 h, 37° C., humidified incubator, the absorbance was analyzed on a VERSAmax microplate reader at 490 nm. Absorbance values were presented as the mean±SE of 3 replicates for each treatment. Cells in controls and compound controls were included. Absorbance of untreated cells was considered 100%.

Assay for Telomerase Activity

Telomerase activity was measured using the modified telomere repeat amplification protocol (TRAP) assay (Wu T C, et al., *Lung Cancer* 2003; 41(2):163-169.). Pelleted cells were lysed with 100 μl of 1×CHAPS lysis buffer (10 mM Tris-HCl [pH 7.5], 1 mM EGTA, 0.5% CHAPS, 10% [v/v] glycerol, 5 mM β-2-mercaptoethanol and 0.1 mM phenylmethylsulfonyl fluoride), incubated on ice for 30 minutes and centrifuged (13,000×g, 4° C., 30 min). Supernatant extracts were quantified for protein using a BSA Protein Assay Kit (Pierce, Ill., USA). TRAP assay was performed as previously described (Falchetti M L, et al., *Nucleic Acids Res* 1998; 26(3):862-863.) with only minor modifications, using a set of primers (TS, SEQ ID No: 8: 5'-AATCCGTCGAGCAGAGTT-3'; ACX, SEQ ID No: 9: 5'-GCGCGGCTTACCCT-TACCCTT-ACCCTAACC-3'; NT, SEQ ID No: 10: 5'-ATCGCTTCTCGGCCTTTT-3') and an internal standard, TSNT (SEQ ID No: 11: 5'-AATCCGTCGAGCAGAGT-TAAAAGGCCGAGAAGCGAT-3') (Naasani I, et al., *Cancer Res* 2003; 63(4):824-830.). Reaction mixtures were incubated (25° C., 30 min) for telomerase-mediated extension and the samples were heated to 85° C. (10 min). Taq polymerase was added and each sample was amplified for 30 cycles of polymerase chain reaction (PCR) amplification (94° C. for 30 seconds, 59° C. for 30 seconds and 72° C. for 90 seconds) in a DNA thermal cycler (GeneAmp PCR System 2400, PerkinElmer Co., Norwalk, Conn., USA). TRAP products were resolved by 12.5% (w/v) non-denaturing polyacrylamide gel electrophoresis (PAGE) and visualized by staining with ethidium bromide. Activity of each sample was normalized to that of 50 ng of total cellular protein. Signal intensity in each lane was measured by an area integration of the first 6 ladders from the bottom of the gel using a MultiImage™ (Alpha Innotech Corporation). Relative telomerase activities were quantified by comparing signal intensities among lane and using the positive control (extract of untreated cells) as 100%.

Isolation of RNA, RT-PCR and Real-Time Quantitative RT-PCR

Total cellular RNA was extracted from cells using the guanidium thiocyante method (Ko J L, et al., *Eur J Biochem* 1995; 228(2):244-249.). First, cDNA was reverse-transcribed from 1 µg total cellular RNA using random hexamer primers and murine leukemia virus reverse transcriptase. One microgram of cDNA was amplified for 35 cycles in a reaction volume of 50 It contained 0.5 units of Taq polymerase (Ex taq, TaKara): 200 mM dNTPS, 10 mM Tris-HCl (pH8.0), 1.5 mM $MgCl_2$, 75 mM KCl and 20 pmole of the hTERT sense and antisense primers (SEQ ID No: 12: 5'AGTTCCTGC ACTGG CTGA TGAGT3', SEQ ID No: 13: 5'CTCGGC-CCTCTTTTCTCTGCG3') (Ito H, et al., *Clin Cancer Res* 1998; 4(7):1603-1608.). The PCR reaction included 5-min denaturation (94° C.) followed by 35 cycles, each consisting of denaturation (94° C., 1 min), annealing (60° C., 1 min) and extension (72° C., 2 min) with a final extension phase (10 min). The hTR sense and antisense primers were SEQ ID No: 14: 5'-TCTAACCCTAACTGAGAAGGGCGTAG-3 and SEQ ID No: 15: 5'-GTTTGCTCTAGAATGAACGGTG-GAAG3' (Liu W J, et al., *Biochem Pharmacol* 2002; 64(12): 1677-1687.), respectively. The PCR reaction included denaturation (94° C., 5 min) followed by 29 cycles, each consisting of denaturation (94° C., 1 min), annealing (60° C., 1 min) and extension (72° C., 2 min) with a final extension phase (10 min). The PCR reaction was performed on a programmable thermal controller instrument-thermal cycler Model 2400.

The amplified fragment was identified and found to possess 328 bps (hTERT) and 136 bps (hTR). Meanwhile, the same amount of cDNA was amplified using specific β-actin including sense and antisense primers (SEQ ID No: 16: CAGGGAGTGATGGTGGGCA, SEQ ID No: 17: CAAA-CATCATCTGGTCATCTTCTC), which were obtained according to the manufacturer's instructions (Life Technologies). The samples were subjected to 25 cycles that included denaturation (94° C., 1 min), annealing (60° C., 1 min) and extension (72° C., 2 min) with a final extension phase (10 min). The products were visualized via electrophoresis on 1.5% agarose gel and stained with ethidium bromide. The present invention confirmed the quality of cellular mRNA according to the intensity of β-actin.

Real time quantitative PCR was performed using Assay-on-demand™ reagent kit (HS00162669 ml-90738 E8, Applied Biosystems, Foster City, Calif.) according to the manufacturer's instructions with analysis carried out on ABI PRISM 7700 Sequence Detector System (Perkin-Elmer Applied Biosystem). Each data point was repeated three times. Quantitative values were obtained from the threshold PCR cycle number (Ct), where the increase in signal associated with an exponential growth of PCR product became detectable. The relative mRNA levels in each sample were normalized to its β-actin content. The relative expression target gene levels equaled $2^{\Delta Ct}$, $\Delta Ct\ Ct_{target\ gene} - Ct_{\beta\ actin}$.

Plasmids, Transient Transfection and Reporter Gene Assay

The hTERT promoter p548 (−548 to +50) cloned upstream of the firefly luciferase reporter in the pGL3-Basic vector (Promega Corp., Madison, Wis.), by following the protocol described in Horikawa et al (Horikawa I, et al., *Cancer Res* 1999; 59(4):826-830.) with a modification. For luciferase assay, cells ($7.5 \times 10^4$) were seeded onto 24-well plates, cultured overnight and transfected with the plasmids described above (1 µg/well) using DEAE-dextran (Amersham-Pharmacia plc, Little Chalfont, Bucks, UK) and the previously described protocols (Lopata M A, et al., *Nucleic Acids Res* 1984; 12(14):5707-5717.). After 24 h incubation, the medium was carefully removed and fresh medium containing various concentrations of reFIP-gts was added to the wells. The cells were treated continuously with reFIP-gts for 24 h. Cells were collected and transcriptional activity was assayed using Luciferase Assay System (Promega, Madison, Wis., USA). A plasmid expressing the bacterial β-galactosidase gene was co-transfected in each experiment to serve as internal control of transfection efficiency.

Western Blot Analysis

Cells were lysed and protein concentration was assayed using Bio-Rad Protein Assay Kit (Bio-Rad, Hercules, Calif., USA). Equal amounts of proteins were subjected to sodium dodecyl sulfate 10% polyacrylamide gel electrophoresis. Fractionated proteins were transferred to Hybond-P membrane. Membranes were blocked in PBS containing 5% nonfat milk and 0.2% Tween 20. For the detection of c-Myc and β-actin, polyclonal anti-c-Myc (Santa Cruz Biotechnology Inc.) (1:200) and monoclonal anti β-actin (AC-40, Sigma, Saint Louis, Mich., USA) were incubated with the membranes overnight at 4° C., followed with anti-rabbit and mouse IgG HRP-linked antibody (Cell Signaling Technology, Beverly, Mass., USA). Blots were then developed using an enhanced luminol chemiluminescence (ECL) reagent (NEN, Boston, USA).

Electrophoretic Mobility Shift Assay

Nuclear extracts (10 µg of protein) were isolated as previously described (Weng M W, et al., *Toxicol Lett* 2004; 151 (2):345-355.). The double-stranded oligonucleotides contained the consensus hTERT-E-box, SEQ ID No: 18: 5'-GGGCTAGCGCGCTCCCCACGTGGCG-GAGGGAAAGCTTCC-3' and antisense SEQ ID No: 19: 5'-GGAAGCTTTCCCTCCGCCACGTGGG-GAGCGCGCTAGCCC-3' of the hTERT promoter. The 5' ends were labeled with biotin. The end-labeled oligonucleotides were mixed with TEN buffer (10 mM Tris HCl, 1 mM EDTA, 0.1 M sodium chloride, pH 8.0) and heated (95° C., 5 min) before gradual cooling at RT for annealing. DNA and protein binding reactions were performed (25° C., 15 min) in 20 µl of reaction buffer (10 mM Tris HCl, pH 7.5, 50 mM NaCl, 1 mM EDTA, 10% glycerol, 1 µg poly(dI-dC), 1 mM dithiothreitol and 10 µM biotin-labeled oligonucleotide probes for E-box) with or without oligonucleotides as competitors. Competitor double stranded oligonucleotides were used at 50-fold molar excess. For competitors of the complexes, nuclear extracts were preincubated with the indicated antibodies at 25° C. for 30 min before addition of biotin-labeled oligonucleotide. DNA-protein complexes were separated from unbound DNA probe on native 6% polyacrylamide gels (80 V in 0.5×TBE buffer). The gels were transferred to positive-charged nylon membrane (Roche). Biotinylated probe and strepavidine biotin peroxidase complex were detected using light shift detection kit (PIERCE).

In Vivo Tumor Xenograft Model

For nude mice xenograft model, male immunodeficient nude mice (BALB/c nu/nu mice) 5-6 weeks old, and weighing 18-22 g, were used. Mice were housed under pathogen-free conditions with a 12 h light/12 h dark schedule, and fed an autoclaved diet with ad libitum access to standard rodent chow (Laboratory Rodent Diet 5001, LabDiet, St. Louis, Mo., USA). To establish A549 tumor xenografts, mice were injected s.c. with $1*10^7$ cells mixed with 75 11 A549 plus 75 11 Matrigel (Collaborative Biomedical Products, Bedford, Mass., USA). Fifteen animals were then randomly divided into three groups consisting of five animals each. The Group 1 (n 4) animals was injected i.p. with PBS and served as controls. The animals in Group 2 (n 4) and 3 (n 4) were injected i.p. with 8 and 32 μg FIP-gts protein, respectively, each week. The day of cell implantation was designated as day 0 and tumor growth and tumor appearance were assessed daily after cell injection. After tumor inoculation for 45 days, the mice were sacrificed and the tumors were taken out for size analysis.

Results

Expression and Purification of Recombinant FIP-gts

To understand the function of FIP-gts, reFIP-gts was expressed in E. coli. The soluble recombinant fusion protein of the expected molecular mass was purified on glutathione affinity column. The GST portion of the reFIP-gts fusion protein was cleaved with thrombin, and reFIP-gts was purified on CM-52 column. The yield of reFIP-gts was about 20 mg/liter of induced culture. ReFIP-gts, purified to homogeneity, had the same IFN-γ stimulatory activity to human peripheral blood lymphocytes as native FIP-gts.

Cell Proliferation Assay of A549 Cells Treated with Recombinant FIP-gts

Previous studies had shown that reFIP-gts exhibits potent mitogenic effects on human peripheral blood lymphocytes and mouse splenocytes (Haak-Frendscho M, et al., *Cell Immunol* 1993; 150(1):101-113.; van der Hem L G, et al., *Transplantation* 1995; 60(5):438-443.). It had also been shown to possess an immunomodulatory effect on normal cells, but reFIP-gts anticancer capability had not been clear. To assess the effects of reFIP-gts on the inhibition of A549 cell proliferation, cells were treated with reFIP-gts 2-8 μg/ml for 48 h (FIG. 4A) and 8 μg/ml for various periods (FIG. 4B).

The results showed that reFIP-gts suppressed the proliferation of A549 cells in a dose and time-dependent manner. Compared with untreated cells, cells treated with reFIP-gts at 4 and 8 μg/ml concentrations showed significant proliferation inhibitions of 20% and 40%, respectively. At the highest dose (8 μg/ml) the 72 h treatment reached a significant inhibition of 60%. With the MRC-5 cell line, however, there was no effect of reFIP-gts on proliferation.

Recombinant FIP-gts Suppresses Telomerase Activity of A549 Cells

Telomerase activity was present in the majority of lung cancers but in normal lung tissues it was not detectable (Lee J C, et al., *Lung Cancer* 1998; 21(2):99-103.). Telomerase activity was altered in reFIP-gts-treated A549 cells could be determined by Using TRAP assay.

Cells were treated with reFIP-gts 2-8 μg/ml for 24 h and 48 h. Compared with untreated cells, the telomerase activity of A549 cells was slight reduction at 24 h and a significantly suppressed after treatment with reFIP-gts 8 μg/ml for 48 h (reduced to 40%) (FIG. 4).

Down-Regulation of Telomerase Catalytic Subunit in reFIP-gts-Treated A549 Cells

The limiting step in telomerase activation was transcription of the catalytic subunit of telomerase, hTERT (Cong Y S, et al., *Microbiol Mol Biol Rev* 2002; 66(3):407-425, table of contents.). To assess changes in hTERT mRNA expression over the course of reFIP-gts-induced telomerase activity decrease, semiquantitative RT-PCR technique is applied to analyze hTERT transcript in freshly collected cells.

hTERT transcription played a crucial role in regulating telomerase activity in reFIP-gts-treated A549 cells. The hTERT mRNA levels in A549 cells were significantly reduced after treatment with reFIP-gts 4 and 8 μg/ml for 12 h (FIG. 11A, first panel from the top). reFIP-gts had no effect, however, on the mRNA levels of hTR (FIG. 11A, second panel from the top). The mRNA levels of β-actin were used as internal controls, and their levels were similar in each sample (FIG. 11A). Real-time PCR also confirmed that hTERT mRNA levels in A549 cells were significantly suppressed after treatment with reFIP-gts (FIG. 11B).

Recombinant FIP-gts Down-Regulates hTERT Promoter in A549 Cells

The effect of reFIP-gts on hTERT expression by performing transient transfection assays on A549 cells was determined using the wild-type hTERT promoter-luciferase reporter plasmid hTERT-p-548 carrying the 548 by promoter fragment from hTERT that includes the regions required for basal hTERT transcription (Horikawa I, et al., *Cancer Res* 1999; 59(4):826-830.). hTERT-p-548 was transiently transfected into A549 cells.

The results showed that reFIP-gts inhibited hTERT-p-548 expression in a dose-dependent manner for the lowest (2 μg/ml) and highest (8 μg/ml) concentrations of reFIP-gts; 1.2 and 2.4-fold repressions of hTERT transcriptional activity were observed, respectively (FIG. 12). However, reFIP-gts did not affect β-Gal expression driven by the CMV promoter. These results demonstrated specific suppressant effects of reFIP-gts on hTERT promoter activity.

Recombinant FIP-gts transrepreseed hTERT promoter through E-box located downstream of the hTERT transcription initiation site To elucidate the elements within the hTERT promoter that are involved in the effects of reFIP-gts on A549 cells, a series of constructs containing unidirectional deletion hTERT promoter-luciferase fragments carrying different responsive elements were made. In untreated A549 cells, the plasmid hTERT-p-212 (containing −212 to +50) shows core promoter activity (Horikawa I, et al., *Cancer Res* 1999; 59(4):826-830.).

In contrast, cells treated with reFIP-gts (8 μg/ml) significantly inhibited hTERT-p-548, hTERT-p-212 and hTERT-p-196 transcriptional activity (reduced about 2-fold). However, hTERT-p-177 promoter activity was not decreased. The hTERT promoter at −196 to −177 district included canonical c-Myc-responsive E-boxes (CACGTG) through which c-Myc efficiently activated hTERT transcription. The data imply that E-box responsive elements are principally responsible for reFIP-gts-induced repression of the hTERT promoter.

Having demonstrated that reFIP-gts most likely represses hTERT expression via the bHLH-binding site on the hTERT promoter, the effect of reFIP-gts on bHLH c-Myc activation was studied. To test whether reFIP-gts affects expression of c-Myc, the cells were treated with reFIP-gts 2 to 8 μg/ml for 24 h and then used to prepare lysates that were subjected to Western blotting with anti-c-Myc antibody. reFIP-gts did not reduce c-Myc expression.

In an attempt to determine whether reFIP-gts decreased DNA binding activity of c-Myc/Max transcription factor in A549 cells, EMSA was performed using double-stranded oligonucleotide containing the E-box motif (CACGTG) on the hTERT promoter sequence spanning the −173 to −152 region as a probe.

DNA binding activity of c-Myc in A549 nuclear extracts (lane 2) was gradually inhibited by reFIP-gts (lane 5) (FIG. 13). The specificity of c-Myc binding to the E-box region of the hTERT promoter was confirmed by the complete competition of the c-Myc/DNA complex in the presence of cold oligomer containing hTERT E-box region (FIG. 13, lanes 2 and 6, respectively).

The reFIP-gts treatment resulted in inhibition of the interaction between E-box region of the hTERT promoter and c-Myc/Max transcription factor. The presence of c-Myc in the protein-DNA complex was confirmed with the complete competition of the DNA/protein band (lane 7) in response to the incubation of A459 nuclear extracts with rabbit polyclonal c-Myc antibody (Santa Cruz Biotechnology) prior to the addition of the probe on EMSA (FIG. 13).

FIP-gts Suppresses Tumor Growth in A549 Xenograft Nude Mice

To further evaluate the antitumor effect of FIP-gts, an in vivo anti-tumor study was performed using nude mice xenograft model subcutaneously inoculated with A549 cells. Small solid tumors were observed 7 days following cell inoculation. As shown in FIG. 14, the pictures of Group 1, Group 2 and Group 3 A549 xenograft nude mice were shown in FIGS. 14 (a), (b) and (c). The tumors sizes of treatment groups were smaller than the control group. After taken out the tumors, the pictures of the tumors were shown in FIG. 15, the average tumor volume of treatment groups (Group 2 and Group 3, FIGS. (b) and (c), for receiving FIP-gts at 8 and 32 μg FIP-gts, n 4) was lower than that of control group (Group 1, FIG. 15(a)) at day 45. Thus, this study had shown that FIP-gts suppresses tumor growth in vivo.

Example 13

Materials and Methods

Animal Strain

BALB/c male mice, 4- to 5-week-old, were purchased from National Laboratory Animal Center in Taiwan.

FIP-gts Dosage

Lower dosage: 200 microgram/kg/day; higher dosage: 600 microgram/kg/day; positive dosage (a commercial Ling-Zhi powder purchased from Taiwan): 300 milligram/kg/day.

Feeding Period, Route and Times

At first, the higher dosage of FIP-gts was formulated. Then, the medium and lower dosage groups were diluted from the higher dosage group. From the first day for test, each group was fed with test materials by oral route once a day over 6 weeks.

Assay

1. Natural Killer Cells Activity

After feeding FIP-gts experimental animals over six weeks, splenocytes was took out from the animals. Assay of natural killer cells activity by flowcytometry was made to compare various dosages groups with negative control group to check whether there was difference between the groups.

2. Macrophages Activity

After feeding FIP-gts experimental animals over six weeks, macrophages in abdomen were took out from the animals. E. coli were labeled with fluorescence. Then, the macrophages were made to phagocytise the labeled E. coli. Assay of the macrophage activity by flowcytometry was made to compare various dosages groups with negative control group to check whether there was difference between the groups.

3. Production of Serum Antibody

During feeding FIP-gts, animals' blood was collected before FIP-gts treated and animal sacrifice. The concentrations of various immunoglobulins in serum were determined and various dosages groups with negative control group were compared to check whether there was difference between the groups.

Result

1. Natural Killer Cells Activity

After sacrificed, the splenocytes of mice were taken from to proceed with assay of natural killer cells activity. To compare with negative control group, each group showed no statistical significance under the ratio of Effector/Target (E/T ratio) was 12.5. To compare with negative control group, higher dosage group and positive control group showed significant differences under E/T ratio was 25.0. To compare with negative control group, lower dosage group, higher dosage group and positive control group showed significant differences under E/T ratio was 50. It appeared that FIP-gts promoted the activity of natural killer cells (Table 7).

TABLE 7

| Group | animal number | E/T ratio | | |
|---|---|---|---|---|
| | | 12.5 | 25.0 | 50.0 |
| A | 10 | 17.5 ± 8.69 | 25.5 ± 8.16 | 26.9 ± 6.57 |
| B | 10 | 25.7 ± 8.59 | 34.9 ± 8.20* | 38.8 ± 6.80* |
| C | 10 | 23.9 ± 10.52 | 32.8 ± 7.92* | 38.1 ± 7.66* |
| D | 10 | 25.2 ± 9.85 | 33.9 ± 10.16* | 38.7 ± 9.22* |

This test is directed to the cytotoxicity assay of natural killer cells identified by flowcytometry.
The symbol (*) indicates statistical significance, as compared with negative control group.
E means effector cell.
T means target cell.
A means negative control group.
B means lower dosage group.
C means higher dosage group.
D means positive control group.

2. Macrophage Activity

After sacrificed, the macrophages in abdomen of mice were collected. FITC-E. coli were added to make phagocytosis by the macrophages. Then, the activity of the macrophages was analyzed by flowcytometry. To compare with negative control group, the lower dosage group and higher dosage group showed statistical significance under Multiplicity of infection (MOI) 30. It appeared that FIP-gts promoted the activity of the macrophages in abdomen (Table 8).

TABLE 8

| Group | animal number | MOI 30 | MOI 50 |
|---|---|---|---|
| A | 10 | 42.17 ± 8.89 | 46.33 ± 12.57 |
| B | 10 | 54.85 ± 8.73* | 52.30 ± 9.05 |
| C | 10 | 53.09 ± 15.73* | 49.74 ± 9.18 |
| D | 10 | 51.07 ± 8.43 | 46.11 ± 6.66 |

This test is directed to macrophage phagocytosis identified by flowcytometry.
The symbol (*) indicates statistical significance, as compared with negative control group.
MOI means multiplicity of infection.
A means negative control group.
B means lower dosage group.
C means higher dosage group.
D means positive control group.

3. Production of Serum Antibody

During feeding FIP-gts, animals' blood was collected before FIP-gts treated and animal sacrifice. The concentrations of various immunoglobulins in serum were determined and various dosages groups with negative control group were compared to check whether there was difference between the groups. The concentration of immunoglobulins in serum before treatment demonstrated that immunoglobulin G (IgG) of higher dosage group and positive control group showed statistical significance as compared with negative control group. Various dosages groups of IgM showed no statistical significance as compared with negative control group.

TABLE 9

| Group | animal number | before treatment | animal sacrifice |
|---|---|---|---|
| | | Ig G (µg/ml) | |
| A | 10 | 431.06 ± 103.42 | 980.11 ± 163.89 |
| B | 10 | 504.22 ± 114.57 | 1324.55 ± 249.15* |

TABLE 9-continued

| Group | animal number | before treatment | animal sacrifice |
|---|---|---|---|
| | | Ig M (µg/ml) | |
| A | 10 | 356.87 ± 24.59 | 461.84 ± 103.5 |
| B | 10 | 333.17 ± 54.36 | 500.54 ± 46.09 |

This test is directed to the condition of serum antibody production identified by ELISA.
The symbol (*) indicates statistical significance ($p < 0.05$), as compared with negative control group.
A means negative control group.
B means higher dosage group.

SEQUENCE LISTING

The sequence list of the present invention is submitted in an ASCII text file named "1091-YB-US-SEQUENCE_ST25.txt", created on Mar. 15, 2012, and the file size is 5740 bytes.

What is claimed is:

1. A method for treating prostate cancer, breast cancer, lung cancer, non-small lung cancer or melanoma cancer in a subject in need, comprising administrating an effective amount of an isolated and/or purified polypeptide of a fungal immunomodulatory protein having the amino acid sequence of SEQ ID NO. 1 to the subject.

2. The method according to claim 1, wherein the fungal immunomodulatory protein suppresses a proliferation of the cancer.

3. The method according to claim 2, wherein the suppression is due to down-regulation hTERT.

4. The method according to claim 3, wherein the down-regulation of the hTERT is due to repression of interaction between c-Myc/Max and E-box region of hTERT promoter.

5. The method according to claim 2, wherein the cancer is arrested at G1 phase.

6. The method according to claim 1, wherein the fungal immunomodulatory protein suppresses a mobility of the cancer.

7. The method according to claim 6, wherein the suppression is performed by down regulation of expression matrix metalloproteinases 2 (MMP2) or up regulation of expression tissue inhibitor of metalloproteinases 1 (TIMP1).

8. The method according to claim 1 wherein the subject is a mammal.

9. The method according to claim 8, wherein the mammal is human.

* * * * *